US010130420B2

(12) United States Patent
Basu et al.

(10) Patent No.: US 10,130,420 B2
(45) Date of Patent: Nov. 20, 2018

(54) CATHETER WITH MEMBRANED SPINES FOR PULMONARY VEIN ISOLATION

(71) Applicant: BIOSENSE WEBSTER (ISRAEL) LTD., Yokneam (IL)

(72) Inventors: Shubhayu Basu, Anaheim, CA (US); Sungwoo Min, Fullerton, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 474 days.

(21) Appl. No.: 14/878,671

(22) Filed: Oct. 8, 2015

(65) Prior Publication Data
US 2017/0100187 A1  Apr. 13, 2017

(51) Int. Cl.
*A61B 18/12* (2006.01)
*A61B 18/14* (2006.01)
*A61B 18/02* (2006.01)
*A61B 18/00* (2006.01)

(52) U.S. Cl.
CPC .......... *A61B 18/1492* (2013.01); *A61B 18/02* (2013.01); *A61B 2018/0022* (2013.01); *A61B 2018/00285* (2013.01); *A61B 2018/00375* (2013.01); *A61B 2018/00577* (2013.01); *A61B 2018/00839* (2013.01); *A61B 2018/00994* (2013.01); *A61B 2018/0212* (2013.01); *A61B 2018/0262* (2013.01);
(Continued)

(58) Field of Classification Search
CPC ................ A61B 18/02; A61B 18/1492; A61B 2018/0022; A61B 2018/00285; A61B 2018/00375; A61B 2018/00577; A61B 2018/00839; A61B 2018/00994; A61B 2018/0212; A61B 2018/0262; A61B 2018/144; A61B 2018/1467; A61B 2218/002
See application file for complete search history.

(56) References Cited

U.S. PATENT DOCUMENTS

| | | |
|---|---|---|
| 3,674,031 A | 7/1972 | Weiche |
| 6,575,933 B1 | 6/2003 | Wittenberger et al. |
| 6,685,732 B2 | 2/2004 | Kramer |

(Continued)

OTHER PUBLICATIONS

European Search Report dated Feb. 22, 2017 from corresponding European Patent Application No. 16192751.2.
(Continued)

*Primary Examiner* — Daniel Fowler

(57) ABSTRACT

A catheter adapted for pulmonary vein isolation, has a distal electrode assembly that can sit stably in an ostium as secured by a plurality of spines and a membrane member. Preshaped and flexible, the spines support the membrane in a concave configuration when the distal electrode assembly approaches the ostium, the spines and membrane member being sized and configured to span across and over the ostium. As the distal electrode assembly is pushed into the ostium, the membrane member elastically deforms, generally turning inside out to expose surface electrodes carried on a contact surface of the membrane member and ring electrodes carried on the spine for contact with the ostium. The membrane member may be inflated. The ring electrodes contact tissue along axial lines of the ostium. The surface electrodes contact tissue along radial lines of the ostium.

4 Claims, 21 Drawing Sheets

(52) U.S. Cl.
CPC . *A61B 2018/144* (2013.01); *A61B 2018/1467* (2013.01); *A61B 2218/002* (2013.01)

(56) References Cited

U.S. PATENT DOCUMENTS

| | | |
|---|---|---|
| 6,905,493 B2 | 6/2005 | Lentz |
| 6,923,808 B2 | 8/2005 | Taimisto |
| 6,997,925 B2 | 2/2006 | Maguire et al. |
| 7,097,643 B2 | 8/2006 | Cornelius et al. |
| 8,128,617 B2 | 3/2012 | Bencini et al. |
| 8,137,342 B2 | 3/2012 | Crossman |
| 8,617,087 B2 | 12/2013 | Schultz |
| 8,747,351 B2 | 6/2014 | Schultz |
| 2003/0093072 A1 | 5/2003 | Friedman |
| 2012/0109116 A1 | 5/2012 | Asconeguy et al. |
| 2013/0053732 A1 | 2/2013 | Heuser |
| 2013/0096550 A1* | 5/2013 | Hill .................... A61B 18/1492 606/33 |
| 2014/0276724 A1 | 9/2014 | Goshayeshgar |
| 2015/0216580 A1 | 8/2015 | Mihalik |

OTHER PUBLICATIONS

U.S. Appl. No. 13/860,921, filed Apr. 11, 2013.
U.S. Appl. No. 14/063,477, filed Oct. 25, 2013.

\* cited by examiner

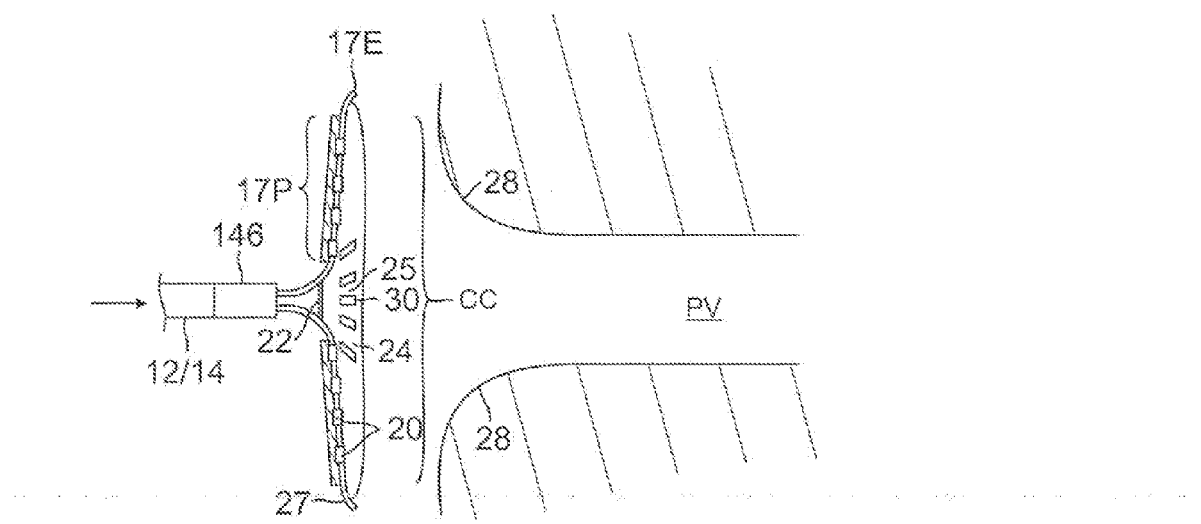
FIG. 3A
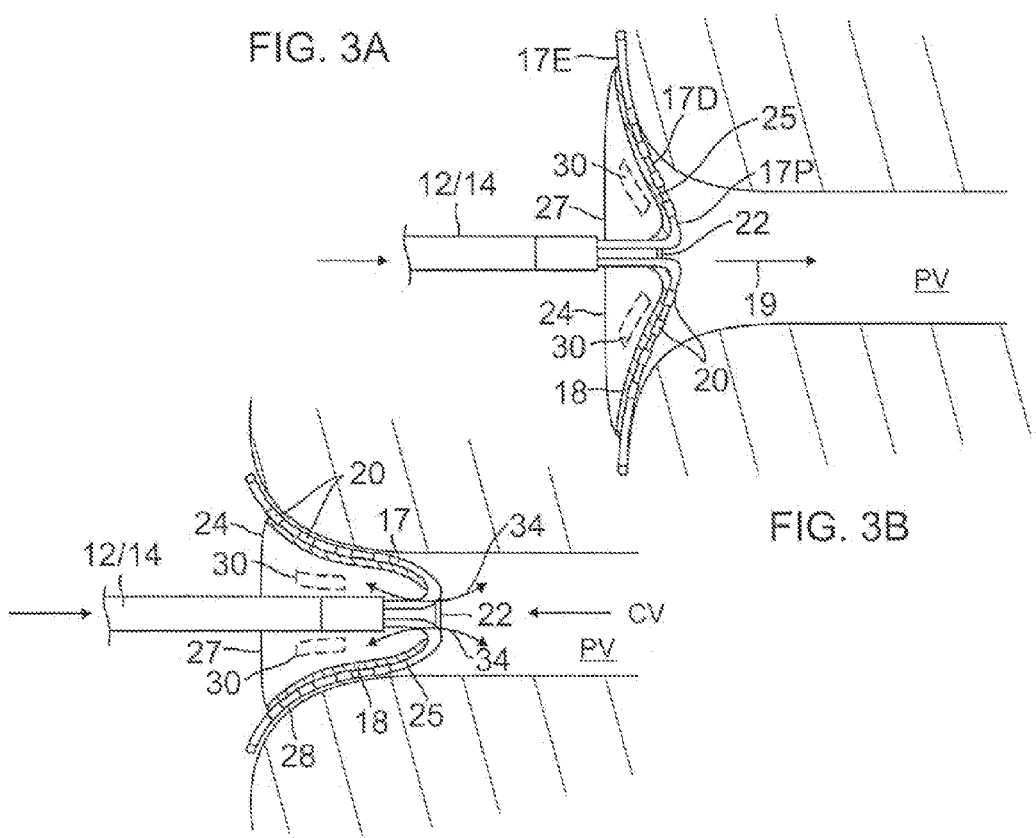
FIG. 3B
FIG. 3C

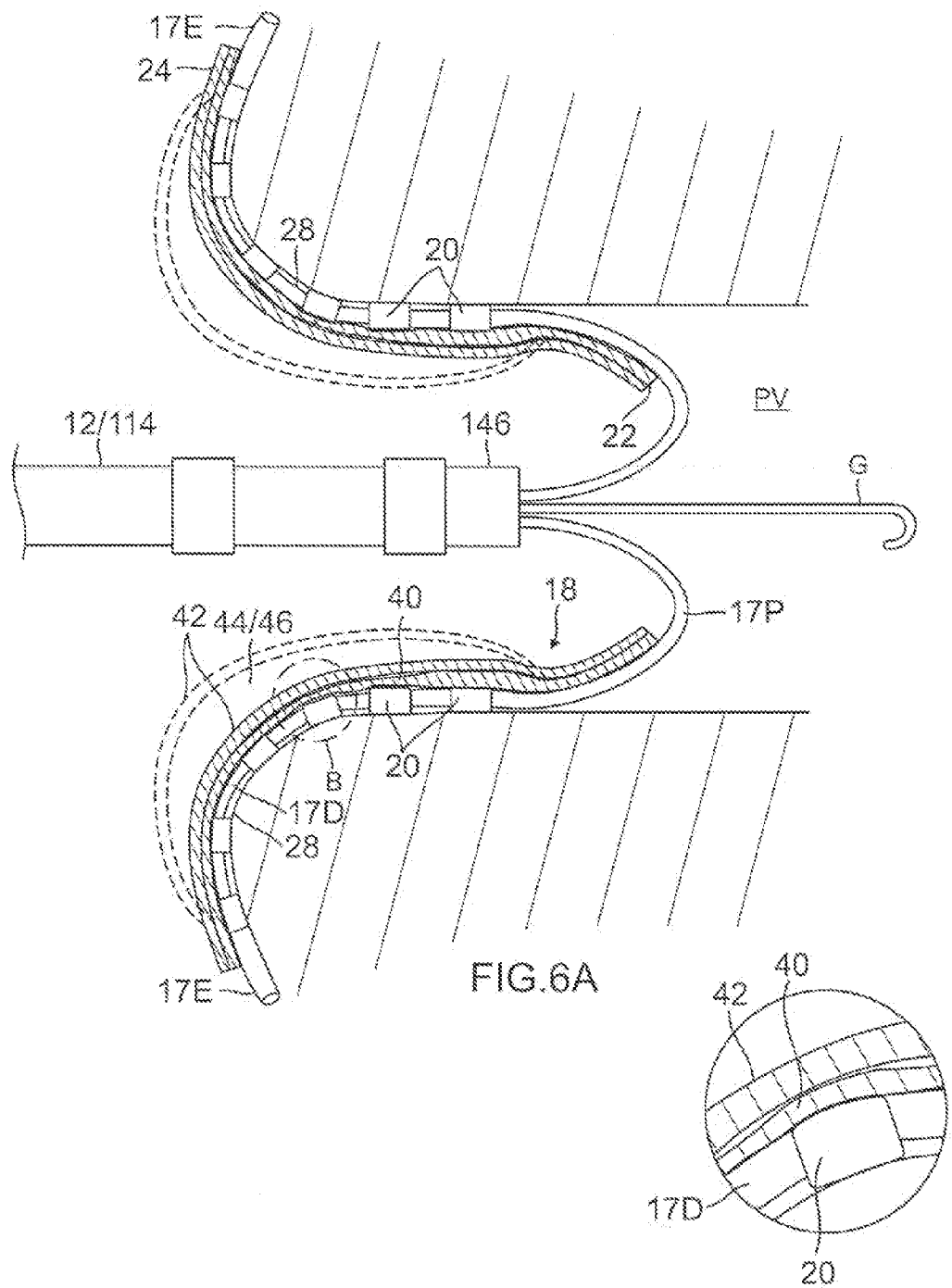

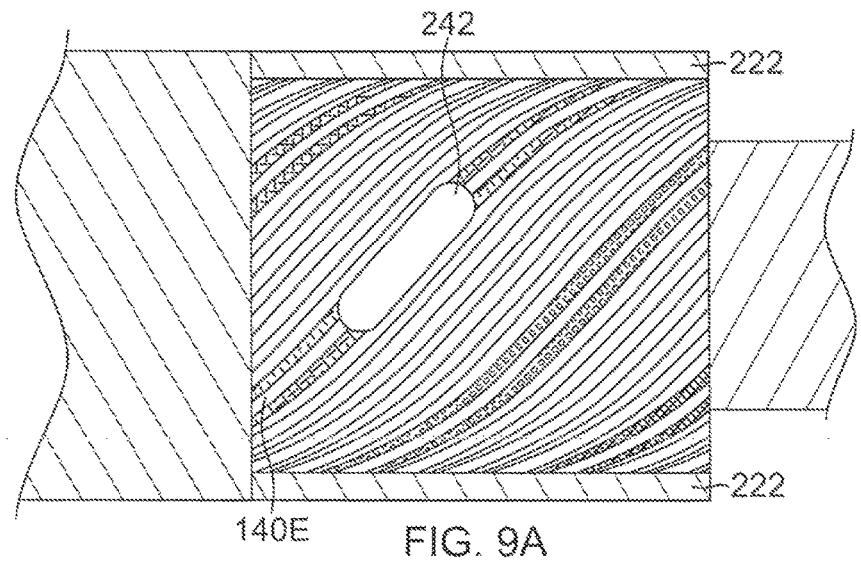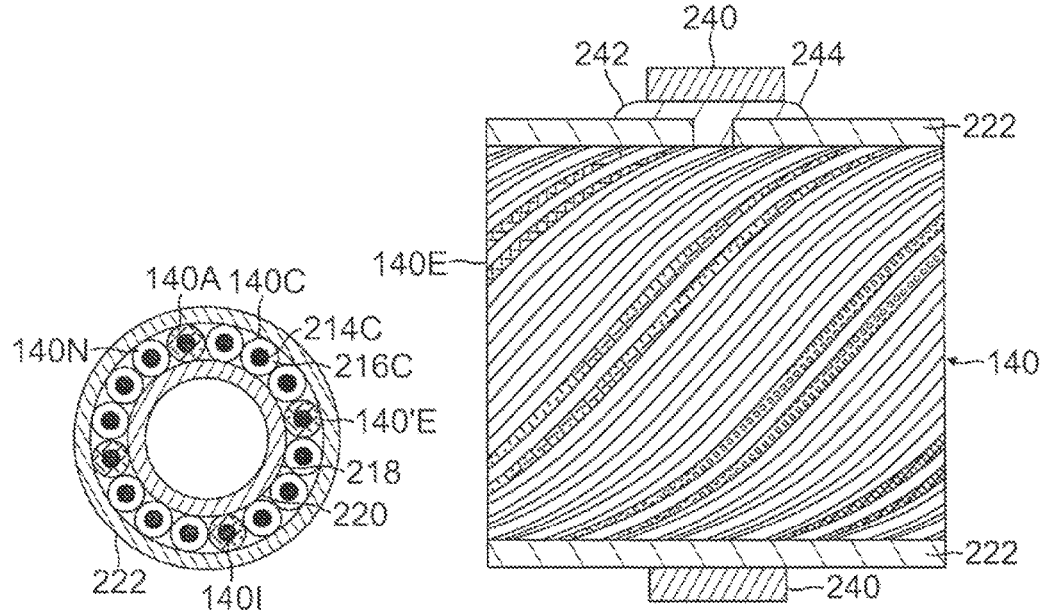

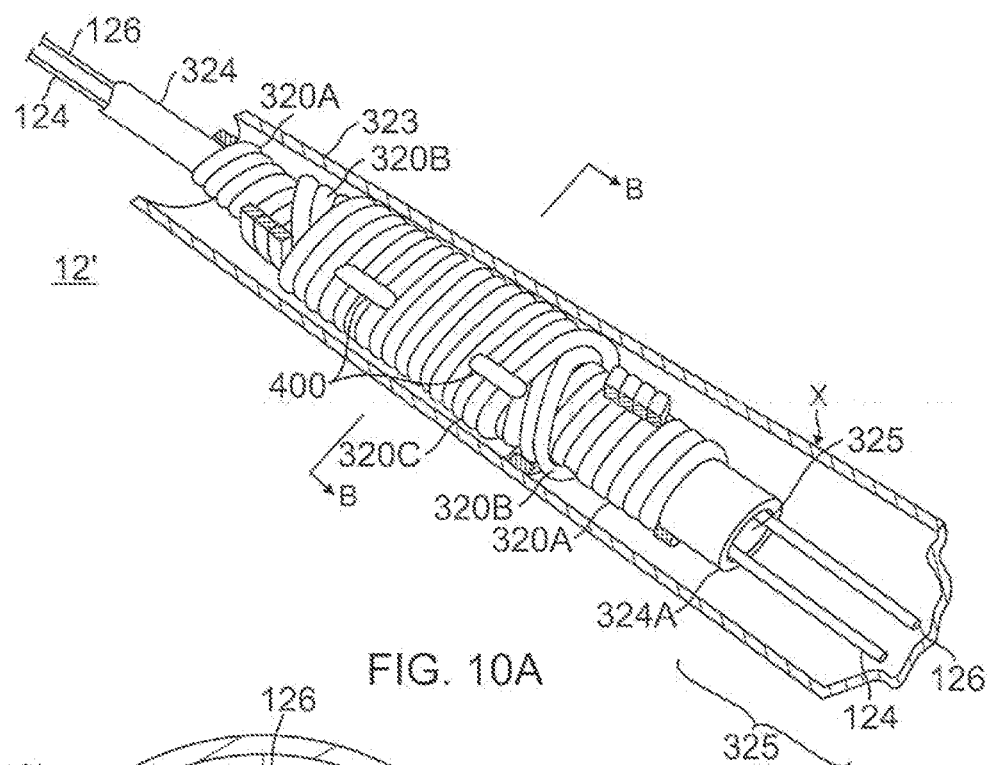
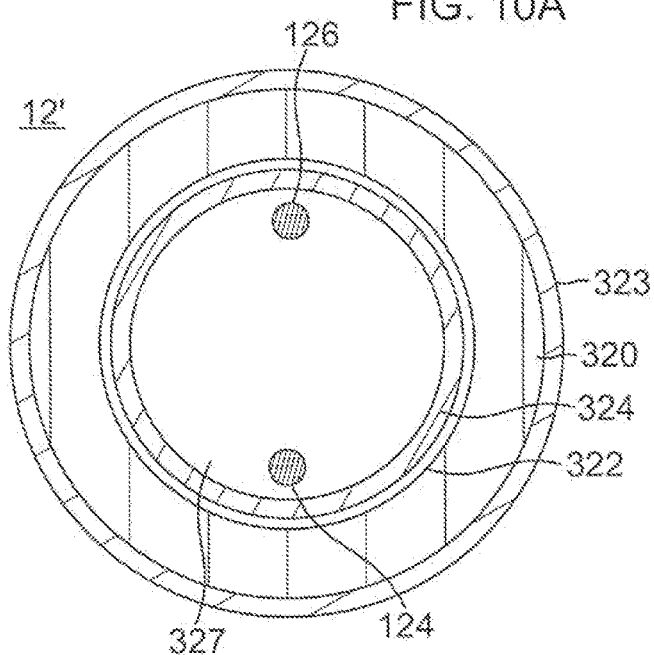
FIG. 10A
FIG. 10B

1

CATHETER WITH MEMBRANED SPINES FOR PULMONARY VEIN ISOLATION

FIELD OF INVENTION

This invention relates to electrophysiologic (EP) catheters, in particular, EP catheters for mapping and/or ablation in the heart.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in various tissue regions in or near the heart, for example, the atria and/or and adjacent structures such as areas of the pulmonary veins, and left and right atrial appendages. Regardless of the sources, unwanted signals are conducted abnormally through heart tissue where they can initiate and/or maintain arrhythmia.

Procedures for treating arrhythmia include surgically disrupting the origin of the signals causing the arrhythmia, as well as disrupting the conducting pathways for such signals. More recently, it has been found that by mapping the electrical properties of the heart muscle in conjunction with the heart anatomy, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In a two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

A typical ablation procedure involves the insertion of a catheter having a tip electrode at its distal end into a heart chamber. A reference electrode is provided, generally taped to the patient's skin. Radio frequency (RF) current is applied to the tip electrode, and flows through the surrounding media, i.e., blood and tissue, toward the reference electrode. The distribution of current depends on the amount of electrode surface in contact with the tissue, as compared to blood which has a higher conductivity than the tissue. Heating of the tissue occurs due to its electrical resistivity. If the tissue is heated sufficiently, cellular and other protein destruction ensues; this in turn forms a lesion within the heart muscle which is electrically non-conductive.

A generally-straight catheter works well, for example, when ablating a line of block in the atria. However, for tubular regions in or around the heart, this type of catheter is cumbersome, skill dependent, and time consuming. For example, when the line of block is to be made about a circumference of the tubular region, it is difficult to manipulate and control the distal end of a straight catheter so that it effectively ablates about the circumference. In current practice a line of block is accomplished by maneuvering the catheter from point to point and is highly dependent on the skill of the operator and can suffer from incomplete isolation of target areas such as the pulmonary vein ostia. However, done well, it can be very effective.

Catheters with circular ablation assemblies (or "lasso-type" catheters) are known. This type of catheter comprises a catheter body having at its distal end an ablation assembly with a preformed generally circular curve with an outer surface and being generally transverse to the axis of the catheter body. In this arrangement, the catheter has at least a portion of the outer circumference of the generally circular curve in contact with the inner circumference or ostium of a tubular region in or near the patient's heart, e.g., a pulmonary vein. However, one drawback with catheters of this type may be the relatively fixed size or circumference of the circular ablation assembly, which may not match the circumference of the tubular region undergoing treatment.

Further, the variance in anatomy observed between subjects makes it difficult for a "one size fits all" approach.

Ablation catheters with expandable assemblies are also known. Such catheters have a circumferential ablation element includes an expandable member with a working length that is adjustable from a radially collapsed position to a radially expanded position. This catheter employs an equatorial band that circumscribes the outer surface of the working length and is adapted to ablate tissue adjacent thereto when actuated by an ablation actuator. However, like most catheters with expandable members, the expandable member is a balloon structure that is inflated with a pressurized fluid source. Inflation of the balloon undesirably restricts blood flow. Added complications may also arise when a balloon is forced to seat in the ostium near the treatment region, such as a pulmonary vein.

Also known is a basket catheter having a basket-shaped electrode array with a mechanism for expanding and retracting the electrode array. The basket assembly has a plurality of spines connected at their proximal and distal ends to an expander that is movable longitudinally to expand and contract the basket-shaped electrode. While this assembly can accomplish circumferential ablation, it may be better suited for mapping and other diagnostic procedures in the chamber areas of the heart. Furthermore, wire spines of basket assemblies can in certain circumstances move or shift relative to each other, rendering the structure of the basket assemblies less stable than desirable.

Accordingly, a need exists for an improved catheter that is particularly useful for circumferential ablation in or near the ostium of tubular regions of the heart. It is desirable that the ablation assembly has a sufficiently stable framework yet be sufficiently pliable and flexible to enable optimal circumferential contact of tissue surrounding an ostium with minimal disturbance or obstruction to blood flow in the region.

SUMMARY OF THE INVENTION

The present invention is directed to a catheter adapted for pulmonary vein isolation, having a distal electrode assembly that can sit stably in an ostium as secured by a plurality of spines and a membrane member. Preshaped and flexible, the spines support the membrane in a generally concave configuration when the distal electrode assembly is deployed and approaches and contacts the ostium, where the spines and membrane member are sized and configured to span across and over the ostium. As the distal electrode assembly is pushed into the ostium, the membrane member elastically deforms, generally turning inside out to expose surface electrodes carried on a contact surface of the membrane member and ring electrodes carried on the spine for contact with the ostium. The membrane member may be inflated to distend and press into contact with the ostium. The ring electrodes of the spines are configured to contact tissue along axial lines of the ostium. The surface electrodes of the membrane member are configured to contact tissue along radial lines of the ostium. The distal electrode assembly can be collapsed from its deployed configuration with the membrane member folded or pleated for advancement through a guiding sheath.

In some embodiments, the catheter has an elongated catheter shaft and a distal electrode assembly shaped much like an umbrella canopy. The catheter shaft defines a longitudinal axis and the distal electrode assembly has a plurality of spines and a membrane member arranged generally symmetrically about the longitudinal axis. Each spine has a free distal end and a proximal end anchored in the catheter shaft, and each spine has at least one ring electrode. The membrane member spans over at least a portion of each spine and has a first surface with at least one surface electrode. The spines and the membrane member define a distal concavity when the distal electrode assembly is out of tissue contact, and a distal convexity when the distal electrode assembly is in tissue contact.

In some embodiments, each spine has a proximal curvature away from the longitudinal axis, a distal curvature toward the longitudinal axis, and a distal end with a tighter curvature toward the longitudinal axis.

In some embodiments, the membrane member has an outer peripheral edge, as well as an inner peripheral edge defining an axial passage through the distal electrode assembly.

In some embodiments, the membrane member is configured for inflation with a two layer construction. The two layer construction may be formed from a folded tubular membrane material. The inflatable membrane member may be sealed in portions between adjacent spines to form separate pockets for selective inflation.

In some embodiments, the surface electrodes configured on a tissue contact surface of the membrane member contact tissue along at least one circumferential region of an ostium and each spine has a plurality of ring electrodes configured to contact tissue along a respective axial line of the ostium.

In some embodiments, the membrane member includes bands extending between adjacent pairs of spines to provide support to the surface electrodes. The bands may have a preformed or biased convex or concave configuration.

BRIEF DESCRIPTION OF THE DRAWINGS

These and other features and advantages of the present invention will be better understood by reference to the following detailed description when considered in conjunction with the accompanying drawings wherein:

FIG. 3A, FIG. 3B and FIG. 3C are side cross-sectional views of the distal electrode assembly of FIG. 2A being advanced into a pulmonary vein ostium.

FIG. 6A is a side cross-sectional view of a distal assembly positioned in an ostium, along a first diameter across two opposing spines.

FIG. 6B is a detailed view of the section B of FIG. 6A.

FIG. 9A is a side view of a cabling for use with the present invention, according to one embodiment, with parts broken away.

FIG. 9B is an end cross-sectional view of the cabling of FIG. 9A.

FIG. 9C is a side view of a cabling with a ring electrode, with parts broken away.

FIG. 10A is a perspective view of a catheter shaft, in accordance with another embodiment.

FIG. 10B is an end cross-sectional view of the catheter shaft of FIG. 10A, taken along line B-B.

DETAILED DESCRIPTION OF THE INVENTION

Figure 1:
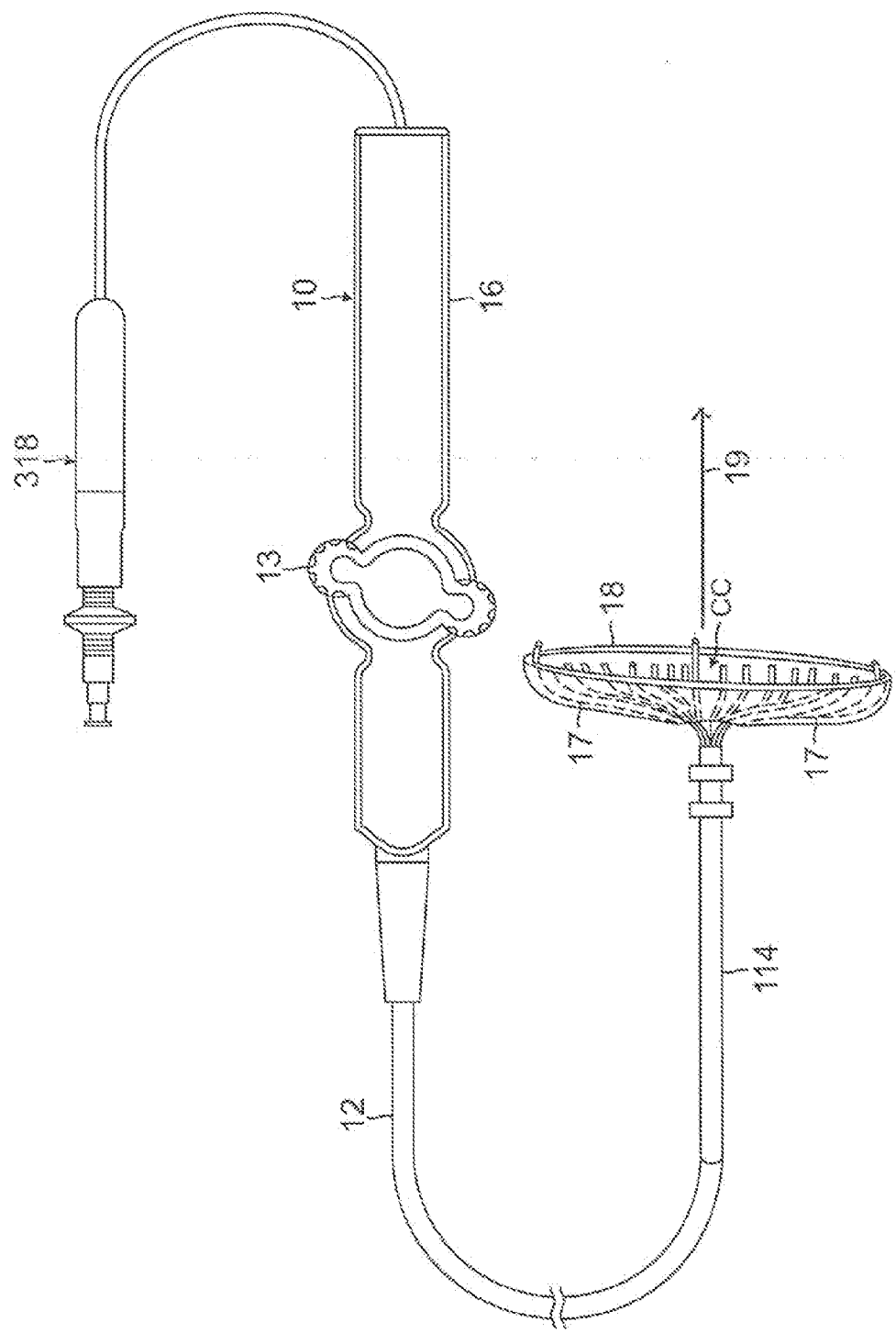
FIG. 1 is a top plan view of a catheter of the present invention, in accordance with one embodiment.
Figure 2A:
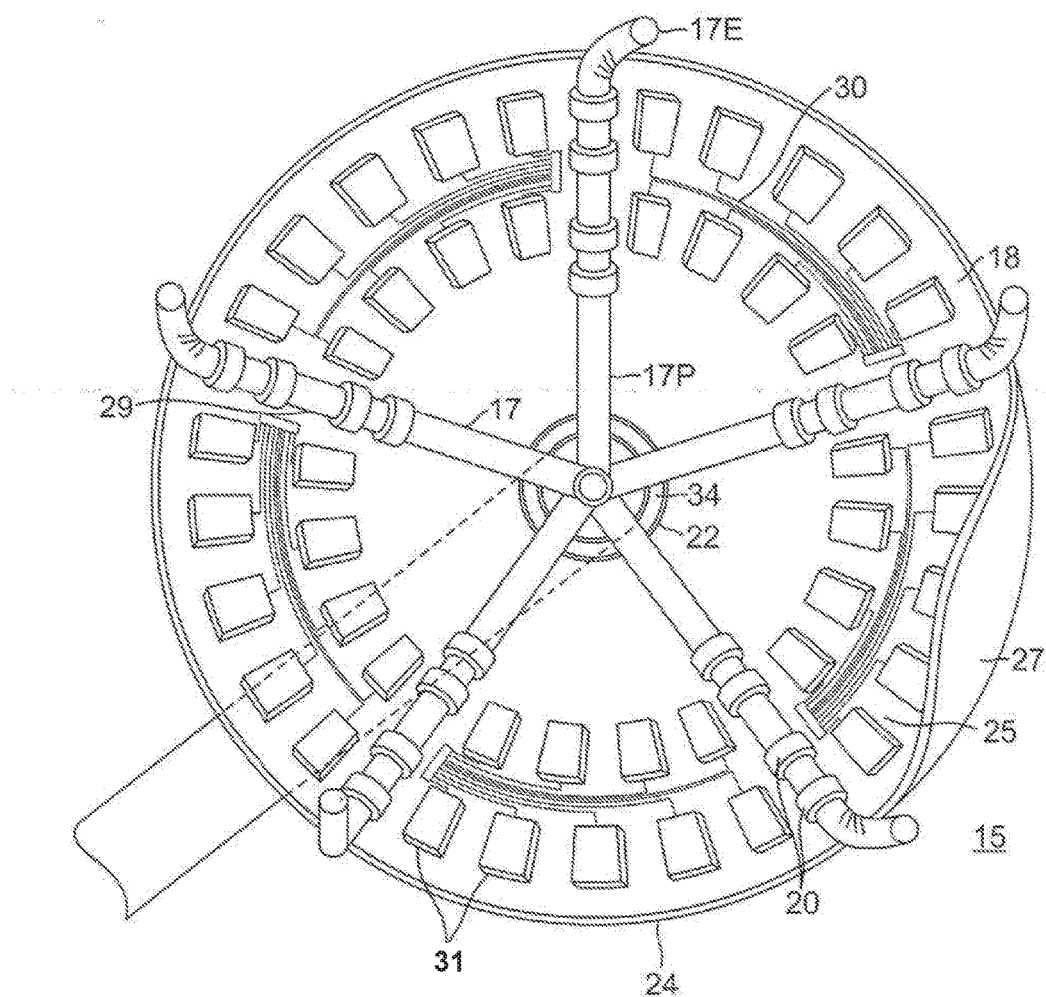
FIG. 2A is an end perspective view of a distal electrode assembly of the catheter of FIG. 1, in a deployed expanded configuration.

As shown in FIG. 1 and FIG. 2A, the catheter 10 comprises an elongated catheter shaft 12, a 3-D distal electrode assembly 15, and a deflection control handle 16 attached to the proximal end of the catheter body 12. In accordance with a feature of the present invention, the distal electrode assembly 15 has a plurality of spines 17 at least partially canopied or covered along their length by a membrane member 18. The spines 17 converge at their proximal ends with their distal ends radiating outwardly from a longitudinal axis 19 of the catheter. The plurality of spines 17 may range between about three and ten, preferably between about five and eight, each at a generally equiangular position about the longitudinal axis 19. For example, where the assembly has five spines, each spine is positioned in increments of about 72 degrees about the longitudinal axis, and where the assembly has ten spines, each spine is positioned in increments of about 36 degrees about the longitudinal axis. In accordance with a feature of the present invention, each spine has a generally similar configuration and is generally symmetrical about the longitudinal axis 19, with a generally straight proximal section 17P, a distal curvature 17D toward the longitudinal axis 19 configured as a "hook," and a distal tip end 17E.

One or more spines 17 carry at least a ring electrode 20. The ring electrodes 20 may be configured for uni-polarity or bi-polarity, as desired or appropriate. The plurality of ring electrodes 20 on each spine 17 may vary, ranging between about four and eight. The ring electrodes may be mapping electrodes and/or ablation electrodes. Where the ring electrodes have ablation capabilities, they may be formed with irrigation pores for irrigation during ablation, as known in the art. In the illustrated embodiment, the ring electrodes are carried on both the proximal and distal portions 17P and 17D of the spines.

In accordance with a feature of the present invention, the membrane member 18 and the spines 17 have similarities in structure to a skirt over a skirt hoop, or a canopy over ribs of an umbrella. In some embodiments, the membrane member 18 has a single layer construction and a "flying disc" shape, with a larger, outer peripheral edge 24 and a smaller, inner center circumferential edge 22 defining a thru-opening or passage 34, as shown in FIG. 2A. The membrane member 18 is laid over the spines 17 such that a front (or inner or distal) surface 25 defines a distal concavity CC as shown in FIG. 1. The membrane member 18 and the spines 17 are affixed to each other along the spine by suitable adhesive or glue. The spines 17 are therefore "webbed" or "canopied" by the membrane member 18, with their proximal ends converging and anchored in the distal end of the catheter shaft 12 (or in a deflection section 114 extending from the catheter shaft 12). Distal ends of the spines 17 are divergent and extend a short distance past the outer peripheral edge 24 of the membrane member 18.

The membrane member material can be of the highly compliant variety, such that the material is elastically flexible and stretches upon application of pressure and takes on the shape of a surface over which it is stretched. Suitable materials include elastomers, such as, for example, silicone, latex, and low durometer polyurethane (for example, a durometer of about 80A). The use of polyurethane is particularly suitable for constructing the membrane member for enabling the assembly 15 to generally conform to the anatomical shape of an ostium 28 of a pulmonary vein 29, as shown in FIGS. 3A-3C.

In FIG. 3A, the assembly 15 is in its deployed configuration with its spines 17 splayed outwardly and the membrane member 18 unfolded to define a distal concavity CC. The assembly 15 is sized such that the outer peripheral edge 24 of the membrane member 18 and the distal ends 17E of the spines are sufficiently wide enough and long enough, to span and cover the ostium 28. In FIG. 3B, as the assembly 15 is further advanced into the ostium 28, the distal ends 17E of the spines and the outer peripheral edge 24 of the membrane member 18 first come in contact with the ostium. As such, the assembly 15 begins to turn inside out, as it begins to invert itself from the distal concavity CC to a distal convexity CV. In FIG. 3C, the assembly 15 passes the ostium 28 and is further advanced into the pulmonary vein PV. The proximal portions 17P and the inner surface 25 of the membrane member now also come into contact with the ostium and inner circumference of the tubular region. With the distal portions 17E "grabbing" onto the ostium 28, the assembly 15 is inverted or turned inside-out with the inner surface 25 now facing outwardly to form the distal convexity CV (and "exposed" much like an inverted umbrella in the wind). An outer/proximal surface 27 of the membrane member 18 now facing inwardly. In this manner, the spines 17 are seated stably in the ostium. The ring electrodes 20 on the spines are pressed into contact with the ostium 28, e.g., for diagnostic mapping. The inner/distal surface 25 of the membrane member 18 is pressed into circumferential contact with the ostium.

In some embodiments, a plurality of surface electrodes 30 are printed or otherwise provided on the inner/distal surface 25 of the membrane member 18, as shown in FIG. 2A. As the assembly 15 is inverted as shown in FIG. 3C, the surface electrodes 30 come into contact with regions of the ostium 28 in between those regions contacted by the spines 17 and ring electrodes 20. Thus, depending on placement and arrangement of the surface electrodes 30 on the membrane member 18, a generally full 360 degree circumferential rings or band of ablation can be achieved around the ostium 28 to provide pulmonary vein isolation.

In some embodiments, the surface electrodes 30 are configured along at least two circumferential closed loops or rings (an outer or larger loop, and an inner or smaller loop) around a center of the membrane member 18, as shown in FIG. 2A. The size and shape of each loop can be varied as desired or needed. The size and shape of each surface electrode 30 can also be varied as desired or needed. For example, each surface electrode 30 can be circular, triangular or any polygonal shape. Each electrode is provided with a respective trace lead 31 on the membrane member 18. All trace leads 31 lead to solder pad 32 suitable for connection with electrode lead wires, as known in the art.

Figure 2B:
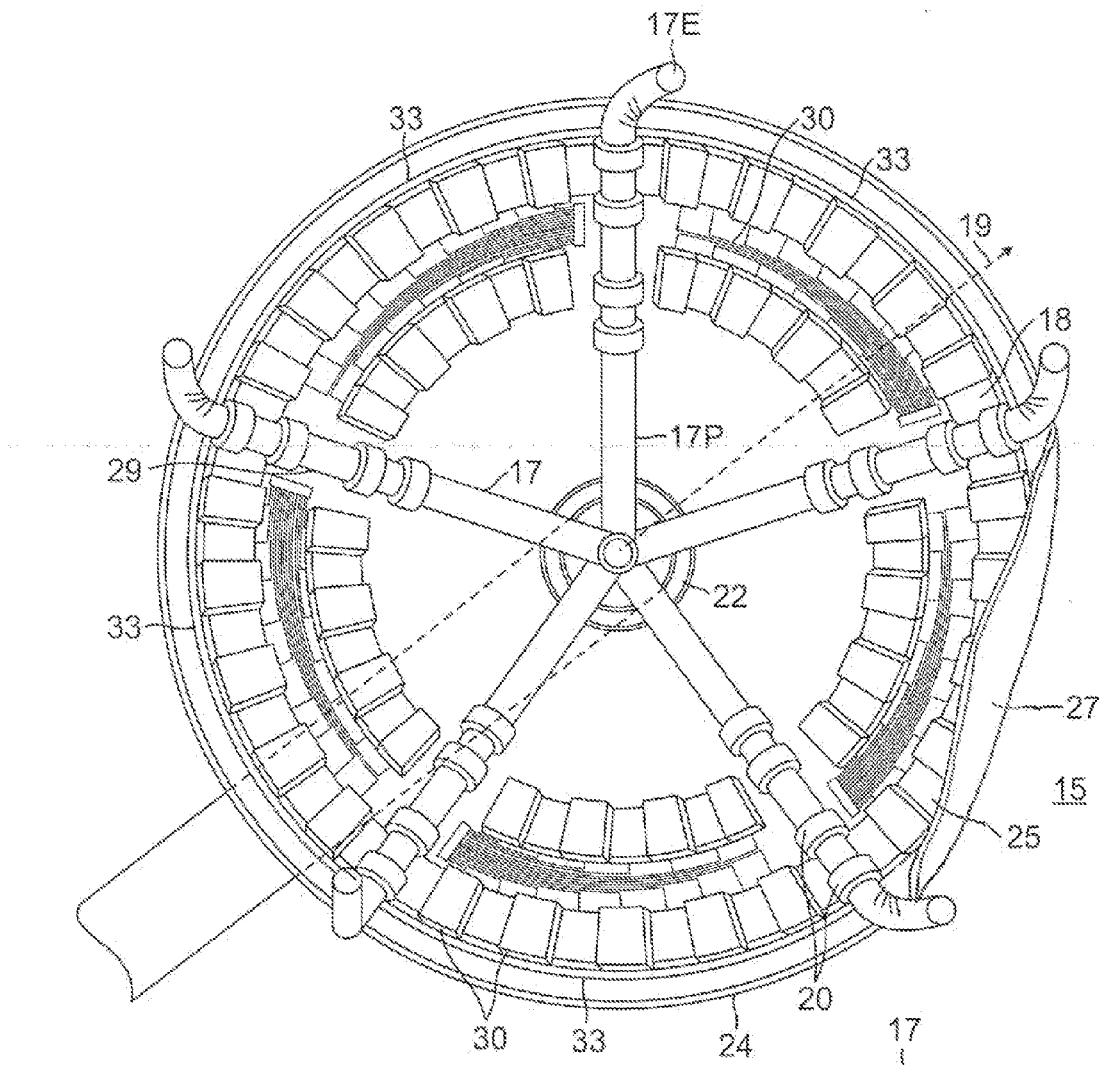
FIG. 2B is an end perspective view of a distal electrode assembly in accordance with another embodiment.
Figure 2C:
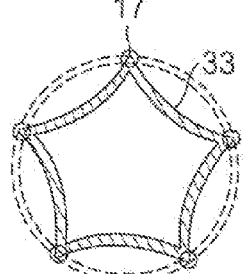
FIG. 2C is an end cross-sectional view of the distal electrode assembly of FIG. 2B.

In other embodiments, the surface electrodes 30 are positioned in immediate proximity with adjacent surface electrodes such that they form a generally continuous surface electrode loops, as shown in FIG. 2B, (with generally even or uneven electrode surfaces, as appropriate or desired). At least one or more elongated support layers or bands 31 spanning between adjacent spines 17 to provide additional support and rigidity to the membrane member 18 in the regions of the surface electrodes 30 may be applied to either surface of the membrane member 18 or embedded therein to ensure contact with the ostium. To that end, the support layers or bands 33 may be configured or preformed with a curvature or flexion. In the embodiment of FIG. 2C, the bands 33 are configured or preformed to bow inwardly. However, it is understood the bands 33 may be configured or preformed to bow outwardly (broken lines in FIG. 2C) in an alternate embodiment.

The assembly 15 when deployed and covering the ostium 28 advantageously provides an axial passage 34 (see arrows in FIG. 3C) defined by the inner circumferential edge 22 of the membrane member 18 for blood flow through the assembly 15. Thus, blood flow can continue from the pulmonary vein into the left atrium during deployment and use of the assembly 15 in the left atrium.

Figure 4A:
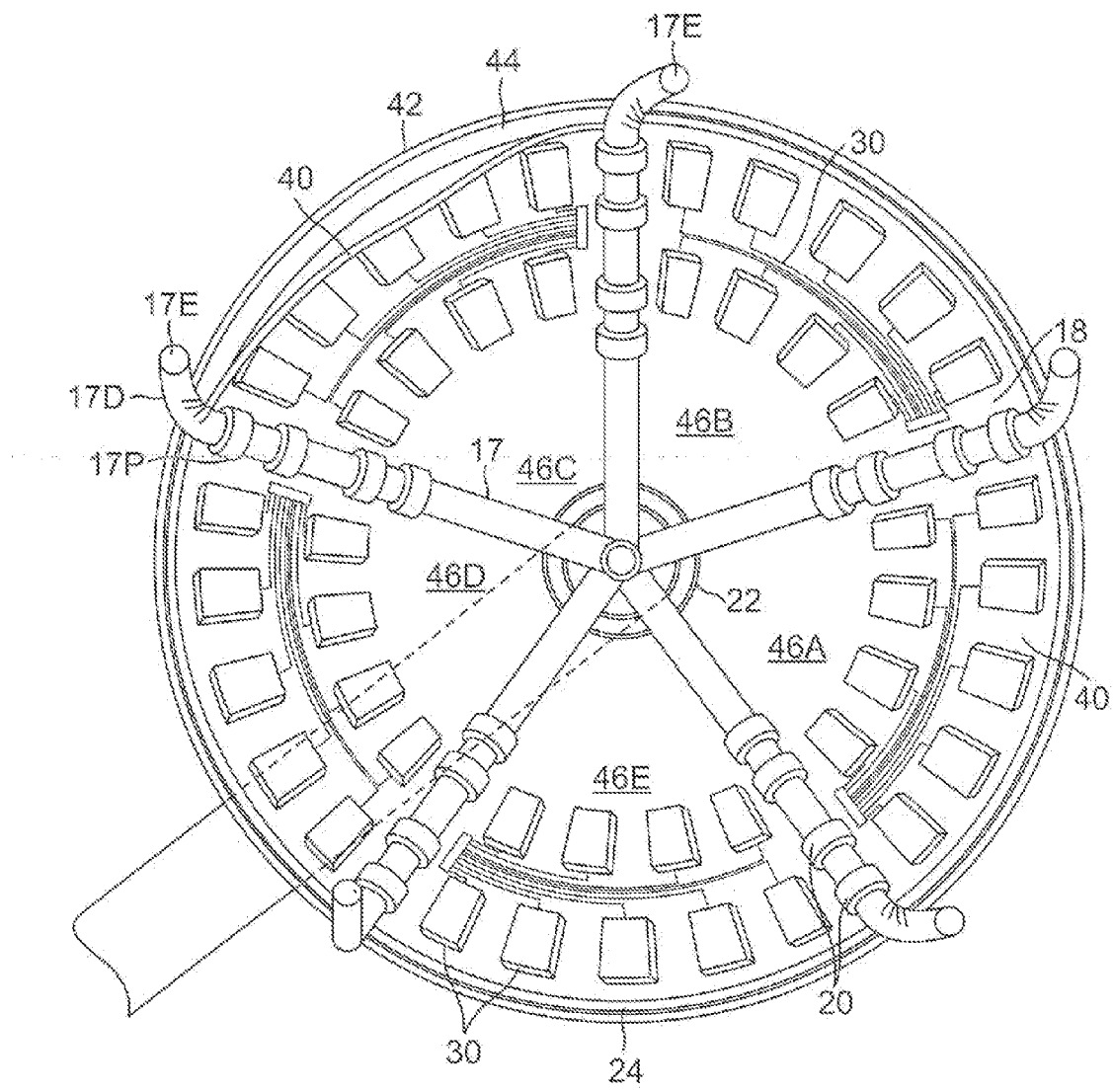
FIG. 4A is an end perspective view of a distal electrode assembly with an inflatable membrane member, in accordance with an embodiment of the present invention.
Figure 4B:
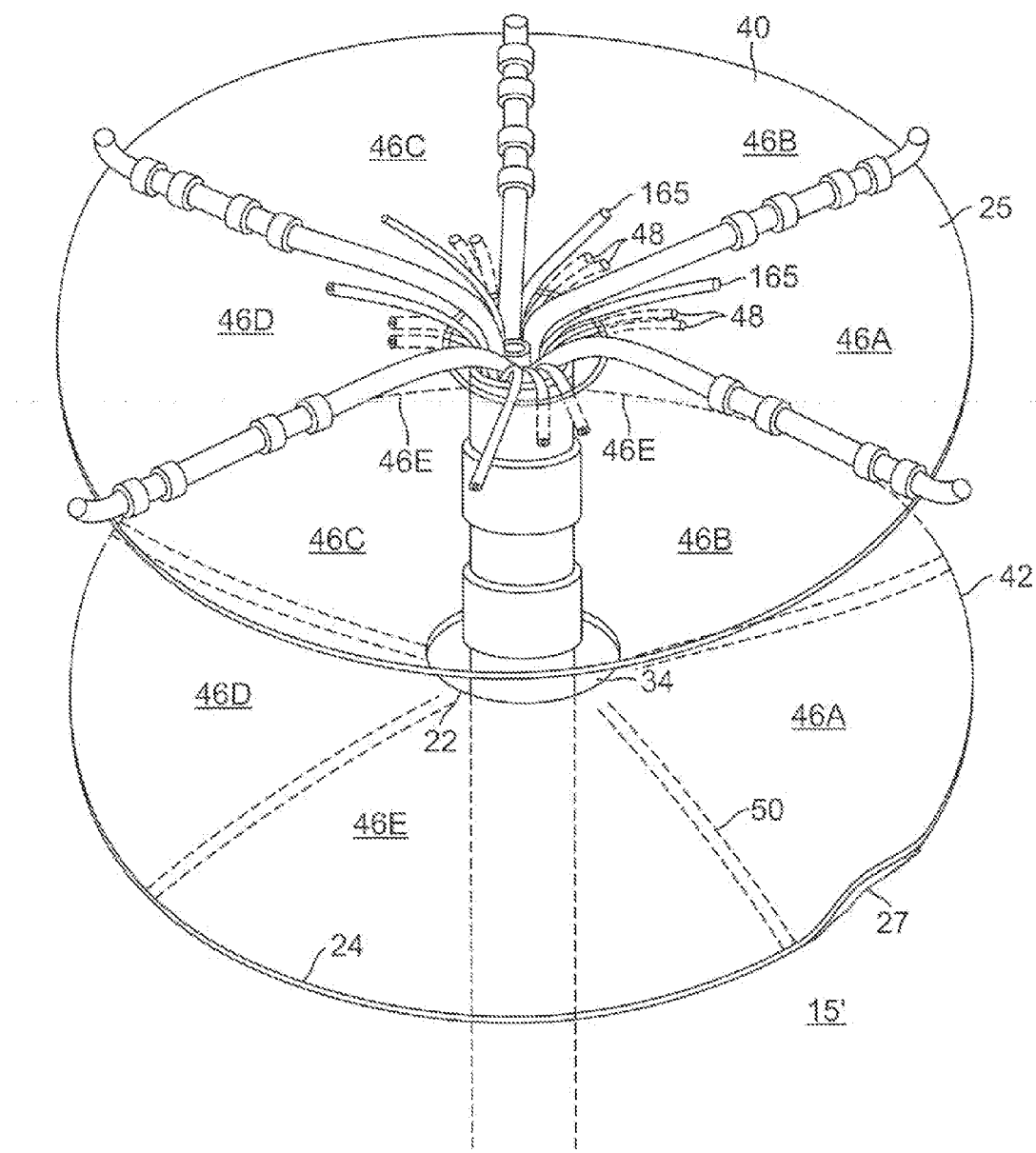
FIG. 4B is an exploded perspective view of the distal electrode assembly of FIG. 4A.

In another embodiment of the present invention, as shown in FIG. 4A and FIG. 4B, a distal assembly 15' has an inflatable membrane member 18' with at least a front (or inner or distal) layer 40 and a back (or outer or proximal) layer 42 between which is provided at least one interior cavity 44 therebetween spanning between the inner peripheral edge 22 and the outer peripheral edge 24. The layers 40 and 42 are sealed by adhesive or other suitable means along their inner and outer peripheral edges 22 and 24 (although it is understood that the layers 40 and 42 are shown partially separated in FIG. 4A solely for purposes of illustrating the cavity 44 therebetween). The interior cavity 44 may be subdivided into a plurality of independent and separate subcavities or pockets 46i (e.g., 46A-46E) in correspondence with a plurality of "i" spines. In the illustrated embodiment, the assembly 15' has five spines and thus five pockets 46A-46E. The layers 40 and 42 are sealed along regions or lines 50 (along periphery edges 22 and 24), as shown in FIG. 4B, to form individual pockets corresponding to the placement and location of the spines 17, and the inner/distal layer 40 on its front face 25 is further affixed to the spines 17 along regions or lines 50. The assembly 15' includes at least one fluid tubing 48 for passing inflation fluid into and out of the inflatable membrane member 15'. In the illustrated embodiment of FIG. 4B, each pocket 46i is in communication with a pair of tubing: a tubing 48A for passing cryogenic fluid into each pocket and a tubing 48B for passing cryogenic fluid out of each pocket 46i. Each tubing 48 has a distal end portion sandwiched in between the layers 40 and 42 of the inflatable membrane member 15' and the respective pocket is sealed around a distal end opening of each tubing 48. Accordingly, individual pockets may be selectively inflated and/or deflated apart from the other pockets.

Figure 4C:
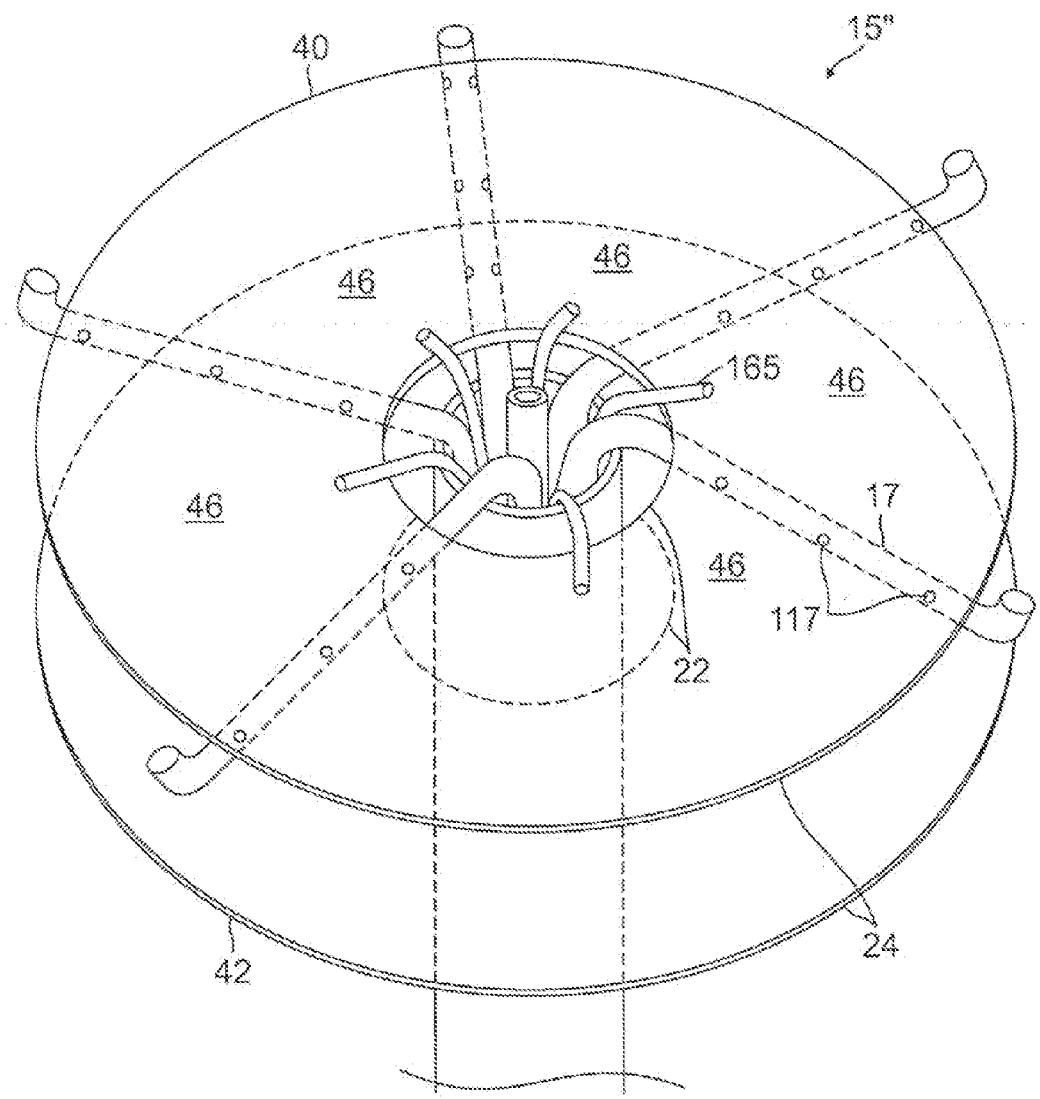
FIG. 4C is an exploded perspective view of a distal electrode assembly in accordance with another embodiment.

In another embodiment of the present invention, as shown in FIG. 4C, an assembly 15" has cryo-irrigated spines 17 formed with a plurality of Gyro-irrigation ports 117 to inflate the pockets 46. Each spine is lumened and in fluid communication at its proximal end with a respective cryo-irrigation tubing extending through the catheter and the catheter shaft and into the assembly 15". Each spine is positioned or sandwiched between the layers 40 and 42 of the membrane. Each pocket 46 is formed by sealing the outer and inner periphery edges 24 and 22 and the layers 40 and 42 to each spine along the length of each spine without obstructing the cryo-irrigation ports 117.

Figure 5A:
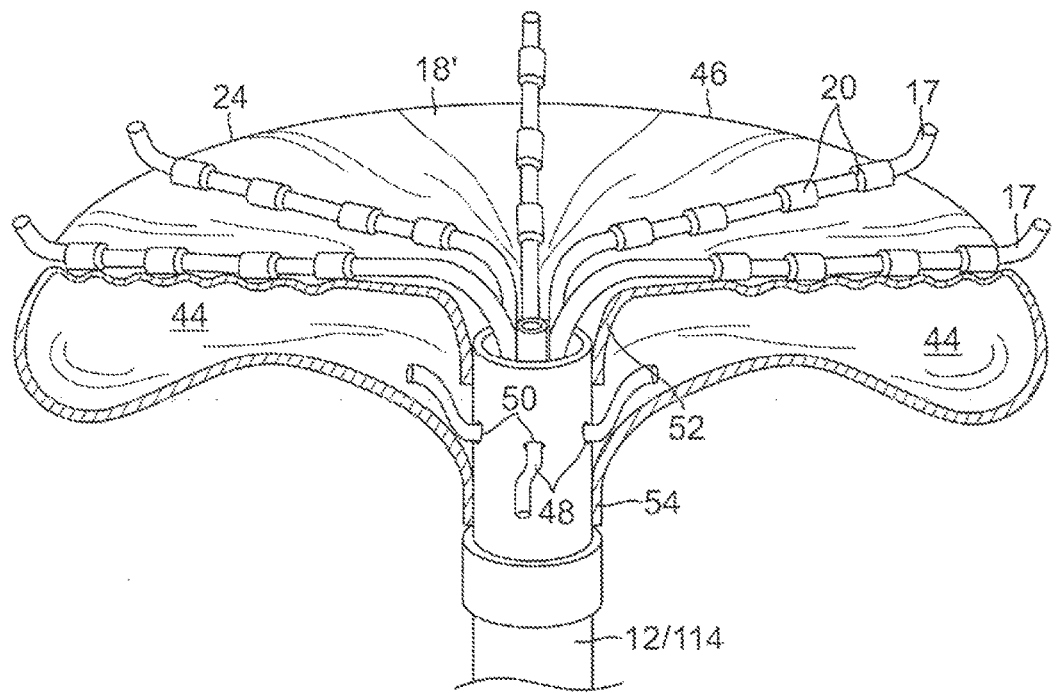
FIG. 5A is a perspective view of a distal electrode assembly with an inflatable membrane member, with parts broken away, in accordance with another embodiment.
Figure 5B:
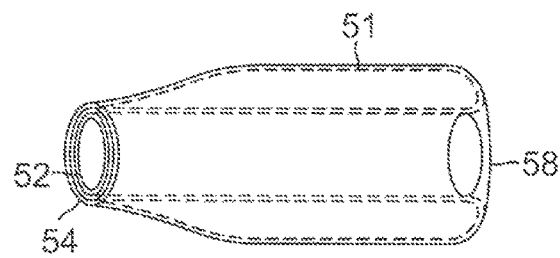
FIG. 5B is a perspective view of a tubular membrane construction of the inflatable membrane member of FIG. 5A.

In another embodiment of the present invention, as shown in FIG. 5A, the inflatable membrane member 18' is formed from a tubular membrane material 51 with a first end 54 and a second end 56, that is folded back on itself along an edge 58, as shown in FIG. 5B, wherein the edge 58 forms the outer peripheral edge 24 of the inflatable membrane member 18'. The first and second ends 54 and 56 may form the inner peripheral edge 22 on the proximal portions 17P of the spines to provide the passage 34, as shown in FIG. 4A. However, in the alternate embodiment of FIG. 5A, the ends 54 and 56 are affixed to the distal end of an intermediate deflection section 114 distal of the catheter shaft 12. In that regard, the fluid tubing 48 in communication with the interior 44 or individual pockets 46 of the membrane member 18' exit the catheter shaft 12 via apertures 50 formed in the shaft 12.

Figure 5C:
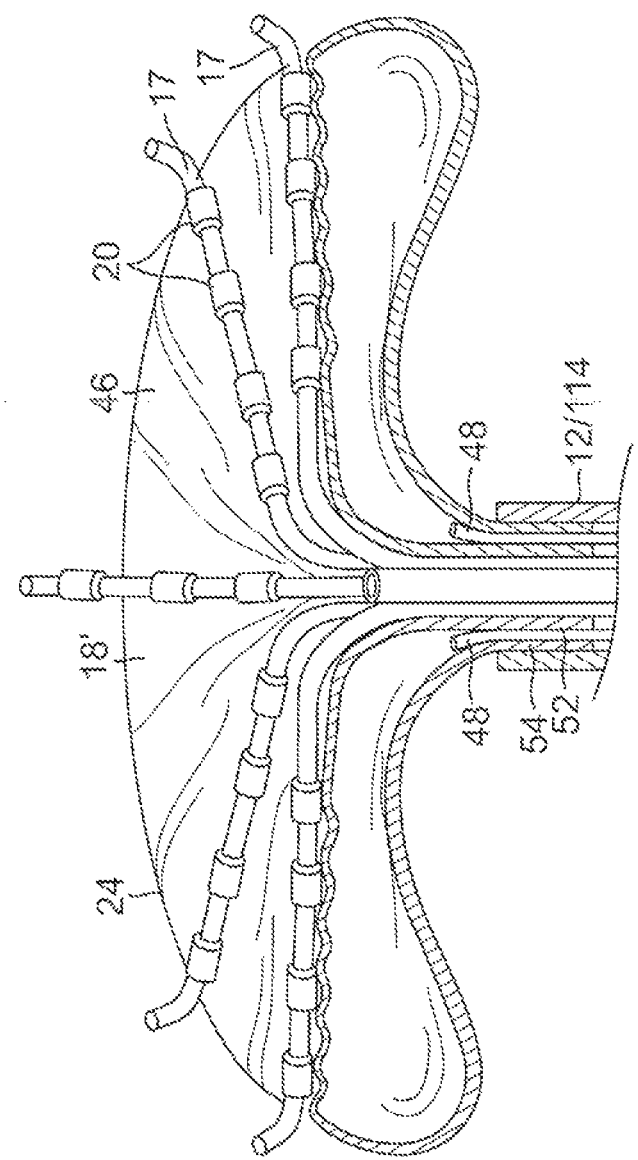
FIG. 5C is a perspective view of a tubular membrane construction in accordance with another embodiment.

In another embodiment, as shown in FIG. 5C, the ends 52 and 54 of the tubular membrane material 51 are received in the distal end of the tubing of the catheter 12 or deflection section 114. Distal ends of the inflation fluid tubings 48 terminate in the interior cavity 44 of the material 51 whose ends 52 and 54 are sealed around the tubings 48 in providing the interior cavity 44 with a fluid-tight seal.

It is understood that the inflatable membrane member may include an outer protective lining or casing as a safety measure in the event the underlying membrane material is punctured, springs a leak or ruptures.

Figure 6C:
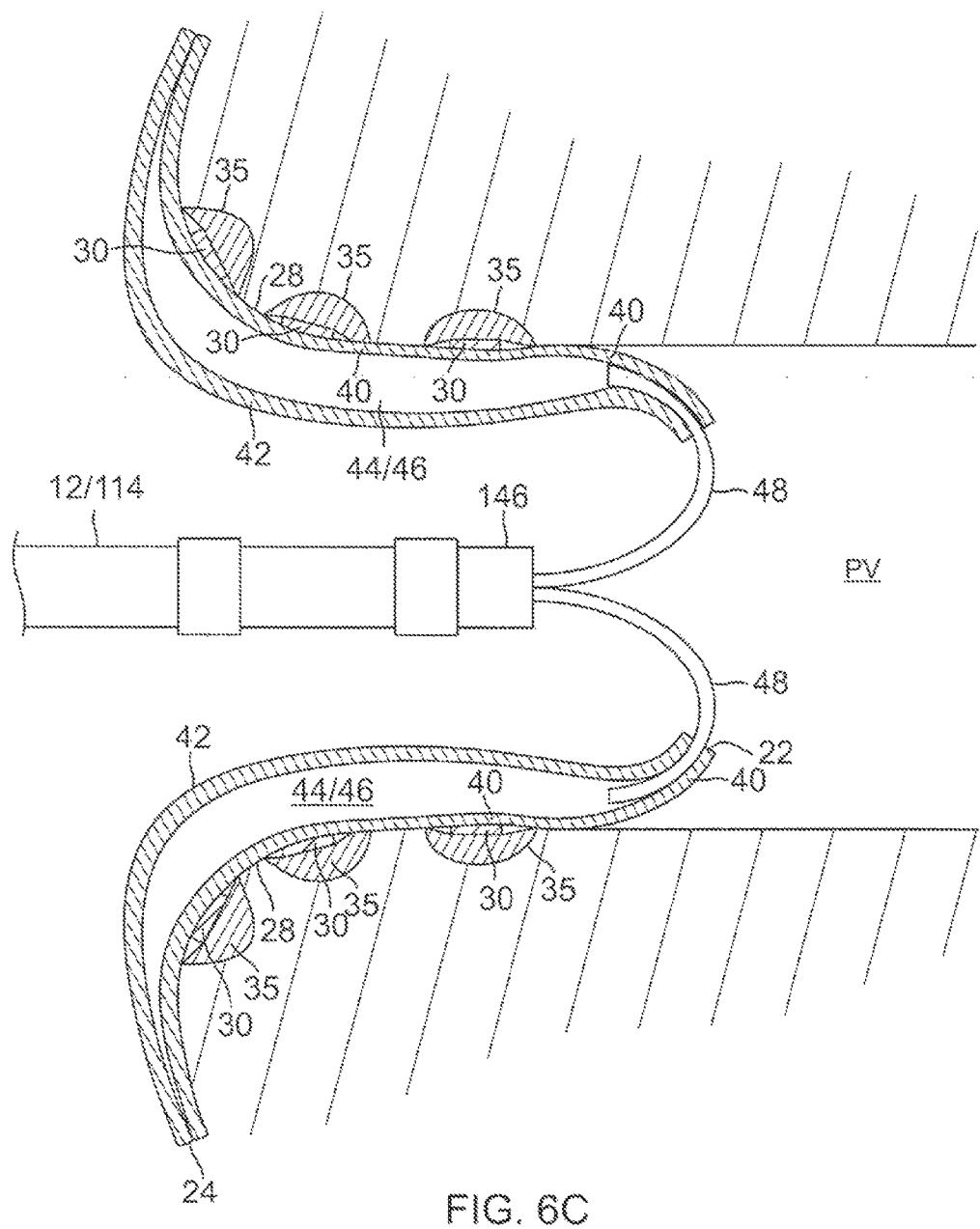
FIG. 6C is a side cross-sectional view of the distal assembly of FIG. 6A, along a second diameter across two opposing pockets of the inflatable membrane member.

When the membrane member 18' is deflated, the ring electrodes 20 on the spines 17 are in contact with the ostium 28, as shown in solid lines in FIG. 6A and FIG. 6B. The ring electrodes 20 may function diagnostically to sense electrically activity of the ostium, for example, for 3-D mapping. When the membrane member 18' is inflated, as shown in broken lines in FIG. 6A and in solid lines in FIG. 6C, for example, with cryogenic fluid, the layers 40 and 42 of the membrane 18' distend and the surface electrodes 30 are pressed into contact with the ostium in regions between the spines 17. The surface electrodes 30 may function therapeutically, for example, for ablating the ostium, with each loop of electrodes 30 ablating a generally contiguous circumferential lesion, e.g., lesion bands 35, to isolate the pulmonary vein. The temperature of the cryogenic fluid inflating the membrane member 18' causes the membrane member 18' to temporarily adhere to the tissue, increasing the stability of the distal assembly 15 in the ostium. The temperature of the cryogenic fluid may also serve to "ablate" tissue in contact with membrane member 18'.

Figure 7:
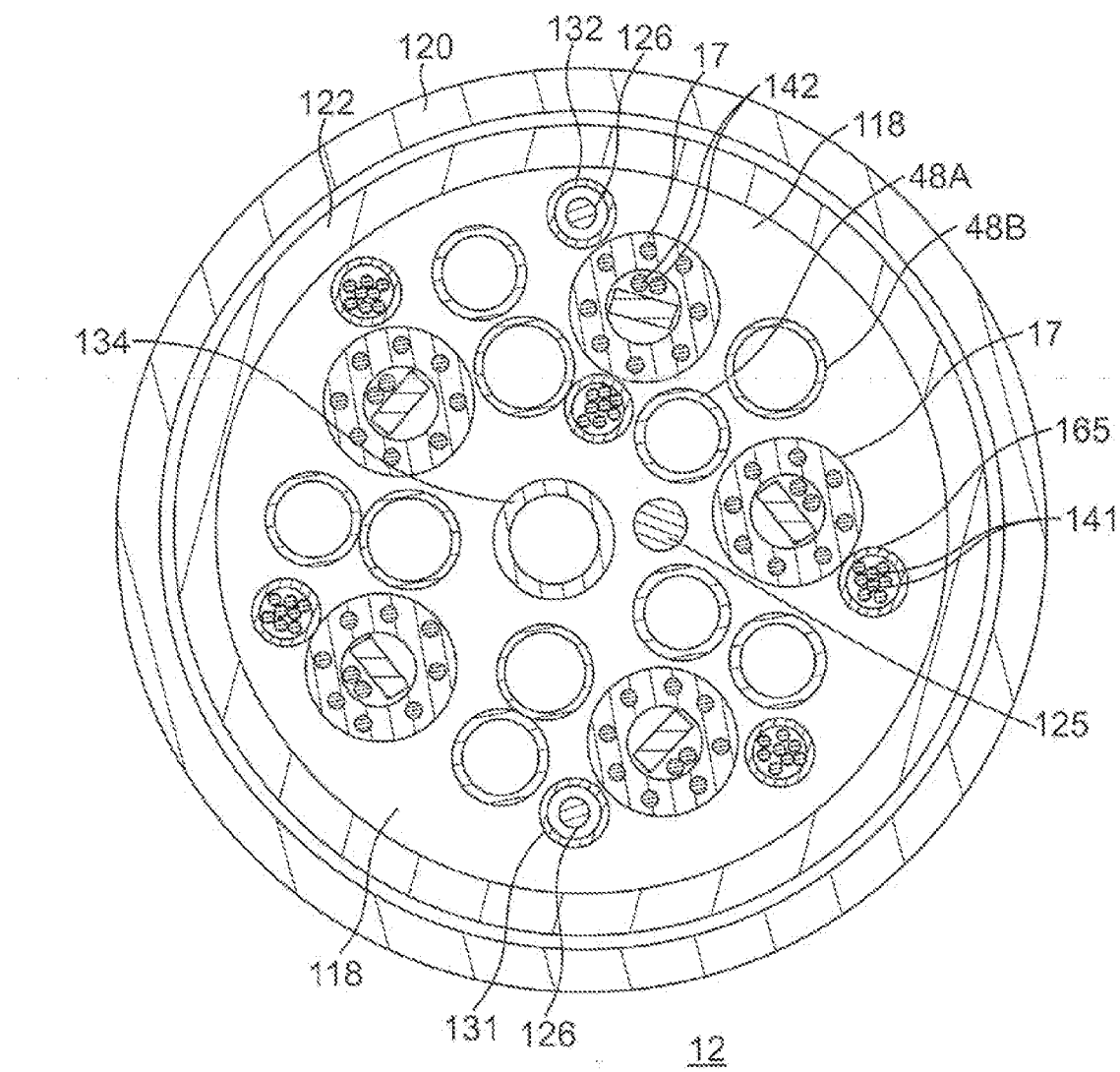
FIG. 7 is an end cross-sectional view of a catheter shaft of the catheter of FIG. 1.

With reference to FIG. 7, the catheter shaft 12 in some embodiments comprises an elongated tubular construction having a single, axial or central lumen 118. The catheter shaft 12 is flexible, i.e., bendable, but substantially non-compressible along its length. The catheter shaft 12 can be of any suitable construction and made of any suitable material. In some embodiments, the catheter shaft 12 comprises an outer wall 120 made of polyurethane or PEBAX. The outer wall 120 comprises an imbedded braided mesh of stainless steel or the like to increase torsional stiffness of the catheter shaft 12 so that, when the control handle 16 is rotated, entire length of the shaft 12 rotates in a corresponding manner.

The outer diameter of the catheter shaft 12 is not critical. Likewise, the thickness of the outer wall 120 is not critical, but is thin enough so that the central lumen 118 can accommodate a variety of components, including one or more puller wires 124 and 126, and their respective compression coils 128, cable 125 (for electromagnetic position sensor 127 housed in or near the distal assembly 15), electrode lead wires 140 (and their cabling 210, described in detail further below), the membrane member inflation fluid tubings 48, a guidewire tubing 134 and any other desired wires, cables or tubes. The inner surface of the outer wall 120 is lined with a stiffening tube 122 to provide improved torsional stability.

In some embodiments, the catheter shaft 12 includes an intermediate deflection section 114 from which the distal assembly 15 extends. In the embodiment illustrated in FIG. 8A and FIG. 8B, the deflection section 114 comprises a shorter section of tubing 119 having multiple lumens, for example, off-axis lumens 131, 132 and a center lumen 133. The first lumen 131 carries the first puller wire 124. The second lumen 132 (generally diametrically opposite of the first lumen 131) carries the second puller wire 126. The third lumen 133 carries the remaining afore-mentioned components. The tubing 119 is made of a suitable non-toxic material that is preferably more flexible than the catheter shaft 12. One suitable material for the tubing 119 is braided polyurethane, i.e., polyurethane with an embedded mesh of braided stainless steel or the like. The size of each lumen is not critical, but is sufficient to house the lead wires, puller wires, the cable and any other components.

Figure 8A:
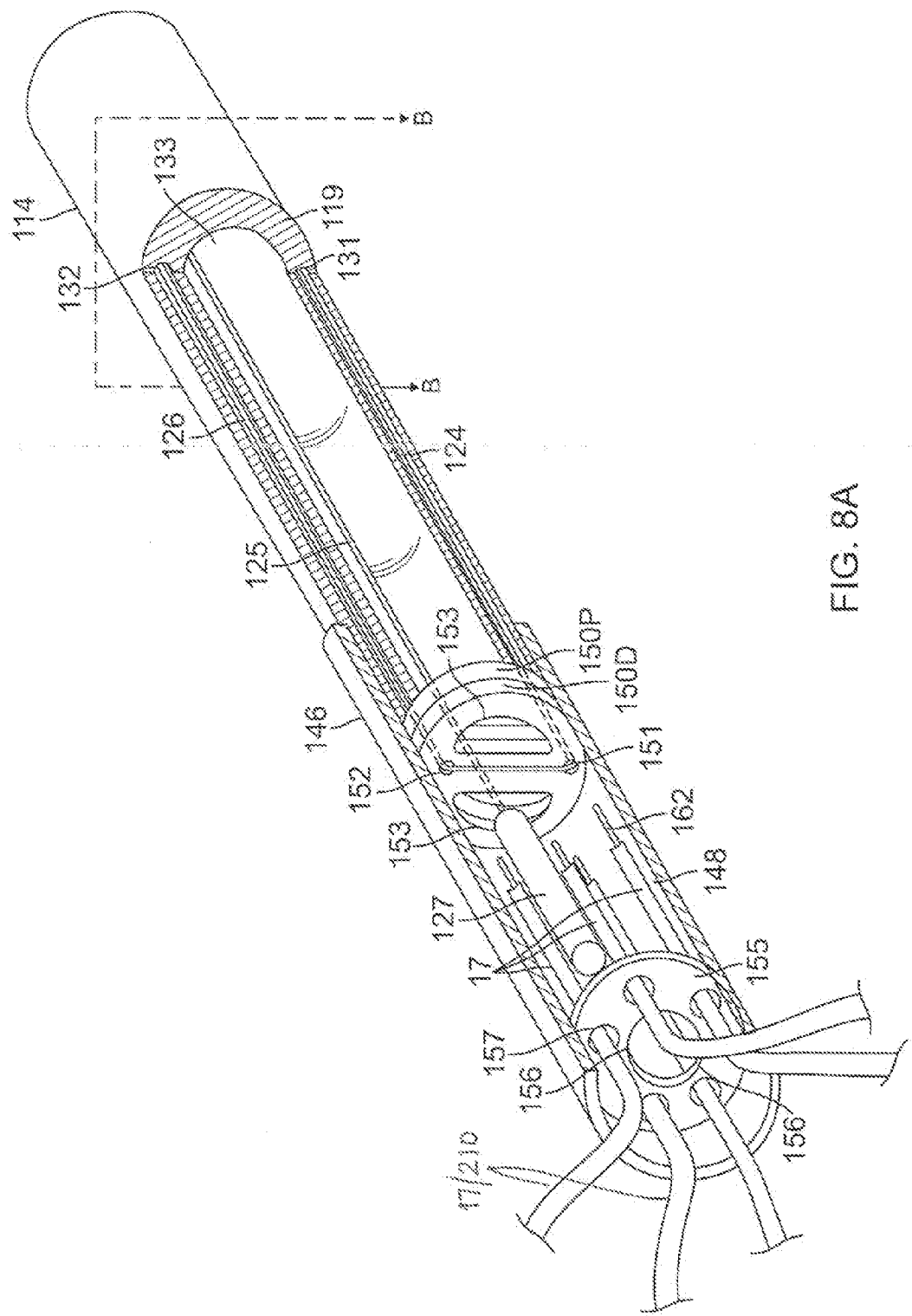
FIG. 8A is a side cross-sectional view of a deflection section and a connector tubing of the catheter of FIG. 1.
Figure 8B:
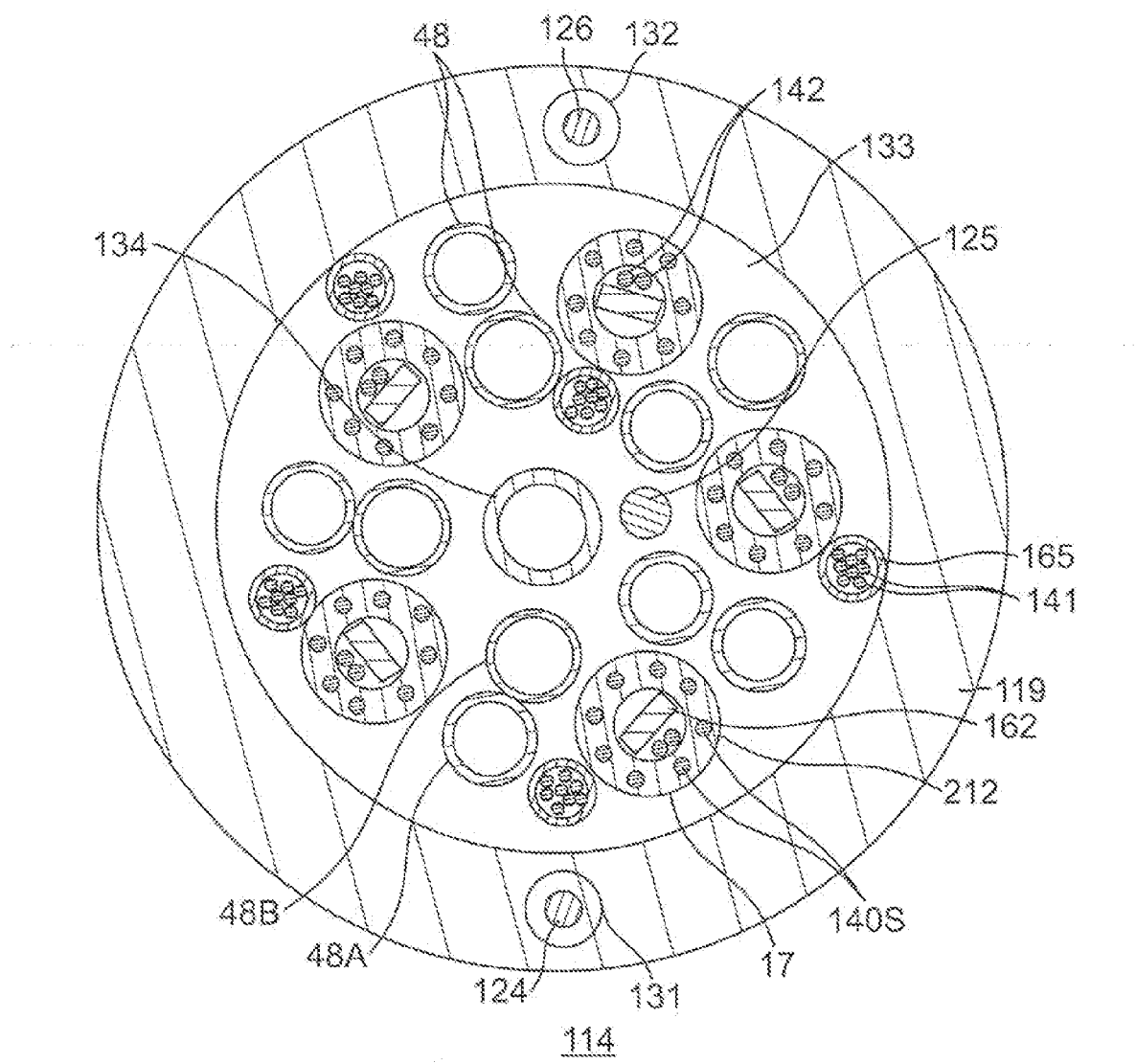
FIG. 8B is an end cross-sectional view of the deflection section of FIG. 8A, taken along line B-B.

A connector tubing 146 extends between a distal end of the deflection section 114 and a proximal end of the distal assembly 15. As shown in the embodiment of FIG. 8A, the connector tubing 146 has a central lumen 148 to house various components, including the electromagnetic position sensor 127, and a distal anchor for the puller wires 124 and 126. In the disclosed embodiment, the distal anchor includes one or more discs, for example, a distal disc 150D and a proximal disc 150P, each of which has a plurality of axial through-holes that allow passage of components between the deflection section 114 and the connector tubing 146 while maintaining axial alignment of these components relative to the lumens 131, 132 and 133. The through-holes include holes 151 and 151 that are axially aligned with the first and second lumens 131 and 132 so as to receive a distal end of puller wires 124 and 126, respectively. It is understood that the puller wires 124 and 126 may be portions of a single tensile member with a distal U-bend section that passes through the holes 151 and 152. With tension on the discs 150D and 150P exerted by the U-bend section of the puller wires 124 and 126, the discs firmly and fixedly abut against the distal end of the tubing 119 of the deflection section 114 to distally anchor the U-bend section.

As shown in FIG. 8A, each disc also includes larger through-holes 153 to allow components to pass between the deflection section 114 and the connector tubing 126. Lead wires (such as lead wires 140 for ring electrodes 20 on the spines 17, and lead wires 141 for surface electrodes on the membrane member 18), the inflation tubing 48, and the sensor cable 125 as between the deflection section 114, and the connector tubing 146 where the electromagnetic position sensor 127 is housed. It is understood that not all of these components are shown in FIG. 8A so as to provide better clarity of the interior of the tubing 119 and the connector tubing 146.

Near its distal end, the connector tubing 146 houses an alignment disc 155 with a center through-hole 156 and a plurality of off-axis through-holes 157. The through-holes 157 are arranged in equi-angular positions around the longitudinal axis of the catheter, each receiving a respective spine 17 to position the spine. Extending through the center through-hole 156 is a distal end of the guidewire tubing 134 (see FIG. 8B).

In the embodiment of FIG. 9A, FIG. 9B and FIG. 9C, each spine 17 comprises a cabling 210 with build-in or embedded lead wires 140 for the ring electrodes 20 on the spines 17. The cabling has a core 218, and a plurality of generally similar wires 140 covered by an insulating layer 216 that enables each wire to be formed and to function as a conductor 214. The core 218 provides a lumen 224 in which can pass other components such as additional lead wire(s), cables, tubing and/or a support structure to shape the cabling as desired. In the illustrated embodiment, an elongated shape memory member 162 extends through the lumen 224 of cabling for each spine 17.

For each spine 17, the support member 162 has a distal end at or near the distal end 17E of the spine and a proximal end at or near the puller wire anchor discs 150P and 150D, as shown in the embodiment of FIG. 8A. However, it is understood that the proximal end of the support member 162 may be anywhere along the length of the spine, as needed or desire. The support member 162 is made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. Thermocouple wire pair 142 may also pass through the core lumen 224 of each spine for measuring the temperature, for example, in the distal end 17E.

In the following description, generally similar components associated with cabling 210 are referred to generically by their identifying component numeral, and are differentiated from each other, as necessary, by appending a letter A, B, C . . . to the numeral. Thus, wire 140C is formed as conductor 214C covered by insulating layer 216C. While embodiments of the cabling may be implemented with substantially any plurality of wires 140 in the cabling, for clarity and simplicity in the following description cabling 210 is assumed to comprise N wires 140A, 140B, 140C, . . . 140N, where N equals at least the number of ring electrodes on each respective spine 17 of the distal electrode assembly 15. For purposes of illustration, insulating layers 216 of wires 140 have been drawn as having approximately the same dimensions as conductors 214. In practice, the insulating layer is typically approximately one-tenth the diameter of the wire.

The wires 140 are formed over the internal core 218, which is typically shaped as a cylindrical tube, and core 218 is also referred to herein as tube 218. The core material is typically selected to be a thermoplastic elastomer such as a polyether block amid (PEBA) or PEBAX.RTM. Wires 140S are formed on an outer surface 220 of the core 218 by coiling the wires around the tube 218. In coiling wires 140 on the surface 220, the wires are arranged so that they contact each other in a "close-packed" configuration. Thus, in the case that core 218 is cylindrical, each wire 140 on the outer surface is in the form of a helical coil. In the case of the tube 218 being cylindrical, the close packed arrangement of the helical coils of wires 140 means that the wires are configured in a multi-start thread configuration. Thus, in the case of the N wires 140 assumed herein, wires 140 are arranged in an N-start thread configuration around cylindrical tube 218.

In contrast to a braid, all helical coils of wires 140 herein have the same handedness (direction of coiling). Moreover, wires in braids surrounding a cylinder are interleaved, so are not in the form of helices. Because of the non-helical nature of the wires in braids, even braid wires with the same handedness do not have a threaded form, let alone a multi-start thread configuration. Furthermore, because of the lack of interleaving in arrangements of wires in embodiments of the cabling, the overall diameter of the cabling produced is less than that of cabling using a braid, and the reduced diameter is particularly beneficial when the cabling is used for a catheter.

Once wires 140 have been formed in the multi-start thread configuration described above, the wires are covered with a protective sheath 222. The protective sheath material is typically selected to be a thermoplastic elastomer such as PEBA, for example, 55D PEBAX without additives so that it is transparent. In that regard, insulating layer of at least one of wires 140 is colored differently from the colors of the remaining wires as an aid in identifying and distinguishing the different wires.

The process of coiling wires 140 around the core 218, and then covering the wires by the sheath 222 essentially embeds the wires within a wall of cabling 210, the wall comprising the core and the sheath. Embedding the wires within a wall means that the wires are not subject to mechanical damage when the cabling is used to form a catheter. Mechanical damage is prevalent for small wires, such as 48AWG wires, if the wires are left loose during assembly of a catheter.

In use as a catheter, an approximately cylindrical volume or lumen 224 enclosed by the core 218, that is afforded by embedding smaller wires (such as the 48 AWG wires) in the wall, allows at least a portion of the lumen 224 to be used for other components. It is understood that the plurality of wires 140 shown in the drawings is representative only and that a suitable cabling provides at least a plurality of wires equal to or greater than the plurality of ring electrodes mounted on each cabling or spine of the assembly. Cabling suitable for use with the present invention is described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which are incorporated herein by reference. Each cabling 210 (with embedded lead wires 140) extends from the control handle 16, through the catheter shaft, and the deflection section 114.

The ring electrodes 20 on the cabling 210 can be made of any suitable solid conductive material, such as platinum or gold, preferably a combination of platinum and iridium, and mounted onto the non-conductive cover 164 and the connector tubing 146 with glue or the like. Alternatively, the ring electrodes can be formed by coating the protective sheath 222 with an electrically conducting material, like platinum, gold and/or iridium. The coating can be applied using sputtering, ion beam deposition or an equivalent technique.

With reference to FIG. 8A, at the proximal end of the assembly 15, the cabling 210 (serving as the spines 27 of the assembly 15, and the terms "spines" and "cabling" being used interchangeably herein) extend through the connector tubing 146 which may be made of any suitable material, for example, PEEK (polyetheretherketone).

In the lumen of the tubing 146, the alignment disc 155 positions the cabling 210. The disc 155 is made of any suitable material, including metal or plastic. Distal of the disc 155, the lumen 148 of the connector tubing 146 is filled and sealed with a suitable glue, e.g., epoxy, applied around the cabling 210 and a distal end of the guidewire tubing 134 (see FIG. 8B) which passes from the tubing 119, through a hole 153 of the puller wire anchor discs 150P and 150, and the hole 156 of the spine alignment disc 155.

For sensing by the ring electrodes 20 of the spines 17, the proximal ends of the lead wires 140 are electrically connected to a suitable connector (not shown) in the distal end of the control handle 16, which is electrically connected to an ECG monitoring system and/or a suitable 3-D electrophysiologic (EP) mapping system, for example, CARTO, CARTO XP or CARTO 3, available from Biosense Webster, Inc. of Irwindale, Calif.

Regardless of the size and number of the ring electrodes 20, the electrode pairs are evenly spaced along each spine in the illustrated embodiment of FIG. 2A and FIG. 2B. The closely-spaced electrode pairs allow for more accurate detection of near field pulmonary vein potential versus far field atrial signals, which can be very important when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the electrophysiologist to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal. However, as understood in the art, the ring electrodes may also be spaced for uni-polar sensing, such as illustrated in FIG. 5A.

The lead wires 141 for the surface electrodes 30 on the membrane member 18 have distal ends which are electrically connected to the solder pads 32 (FIG. 2A and FIG. 2B). The proximal end of the lead wires 141 are connected to a source of ablation energy, e.g., RF energy, which may be provided in a 3-D EP mapping system. A plurality of protective tubing or sheaths 165 surround bundles or groups of the lead wires 141 through the control handle 16, the catheter shaft 12, and the deflection section 114 and into the distal assembly 15. It is understood that the lead wires 141 may be individually connected to each surface electrode 30, or to groups of surface electrodes 30, such as those associated with a particular region or pocket 46 of the membrane member 18 between adjacent pairs of spines 17, such that activation of one lead wire 141 simultaneously activates the associated group of surface electrodes for synchronized ablation by that particular region or pocket 46 of the membrane member 18. The protective sheaths 165 can be made of any suitable material, preferably polyimide.

As illustrated in FIG. 8A, the electromagnetic position sensor 127 is housed in the lumen 148 of the connector tubing 146. The sensor cable 125 extends from a proximal end of the sensor, and through a hole 153 of the discs 150P and 150D, the third lumen 133 of the tubing 119 of the deflection section 114, and the central lumen 118 of the catheter body 12. The cable is attached to a PC board in the control handle 16, as known in the art.

Proximal of the deflection section 114, a compression coil 128 surrounds each puller wire in the catheter shaft 12. Each compression coil has a distal end at or near the proximal end of the deflection section 114, and a proximal end at or near the proximal end of the catheter shaft 12. The compression coils 128 are made of any suitable metal, preferably stainless steel. Each compression coil is tightly wound on itself to provide flexibility, i.e., bending, but to resist compression. The inner diameter of the compression coil is preferably slightly larger than the diameter of its puller wire. A Teflon coating on each puller wire allows it to slide freely within its compression coil. Distal portion of the puller wires past the compression coils 128 may be covered by a flexible, non-conductive sheath (not shown), e.g., made of polyimide tubing, to protect the lumens 131 and 132 from being damaged by the puller wires during deflection.

In an alternate embodiment as shown in FIG. 10A and FIG. 10B, a catheter shaft 12' adapted for deflection in a distal section 325 comprises an outer multi-layered coil member 320 to provide flexibility, torsional stiffness, pushability and rotational accuracy so that when the control handle 16 is rotated, the catheter shaft 12' along its entire length rotates in a corresponding manner.

In some embodiments, the multi-layered coil member 320 includes three layers of compression coils 320A, 320B and 320C, each coil strand or wire having a generally rectangular cross-section, and each coil being wound in a direction different from adjacent layer(s). For example, an inner coil layer 320A and an outer coil layer 320C have a similar winding direction that is different from a winding direction of a middle layer 320B. In the illustrated embodiment of FIG. 10A, the winding direction of the inner coil layer 320A and the outer layer 320C is to the right and the winding direction of the middle layer 320B is generally opposite to the left. Suitable multi-layered coil members are available from Heraeus Medical Components, LLC and sold under the trademark TRIFLEX. An outer covering or shrink sleeve 323, for example, of any suitable biocompatible plastic such as polyurethane or PEBAX, is provided outside of the outer coil layer 320C to protect and provide a fluid-tight sealed interior of the catheter shaft 12'.

The outer diameter of the catheter shaft 12' is not critical. The inner diameter of a central lumen 322 defined by the inner coil layer 320A is not critical, but is large enough so that the central lumen can accommodate at least an inner stiffener member 324 that extends through a proximal portion of the catheter shaft 12' and whose distal end 324D defines a proximal end X of an adjustable deflection section 325 of the catheter shaft 12'.

The stiffener member 324 has a configuration of an elongated lumened tubing that is afforded longitudinal movement relative to the multi-layered coil member 320. The stiffener member 324 has sufficient flexibility for maneuverability within a patient's vasculature but also sufficient rigidity to resist compression and deformity along its length within the central lumen 322 of the coil member 320 so to enable deflection of deflection section 325 in response to the one or more puller wires of the catheter. The stiffener member 324 has an outer diameter smaller than the inner diameter of the central lumen 322, and an inner diameter that is sufficiently large so that its central lumen 327 can accommodate the various aforementioned components.

To actuate the puller wires 124 and 126, an operator manipulates a deflection rocker arm 13 on the control handle 16, as shown in FIG. 1. As known in the art, the arm 13 draws on one or the other puller wires depending on the direction of rotation which deflects the distal section 325 of the catheter shaft in that direction. The type or degree of deflection curvature of the catheter is set by a longitudinal position of the stiffener member 324 relative to the multi-layer coil member 320, which is adjustable by an operator via a deflection curvature adjustment handle 318.

Figure 11:
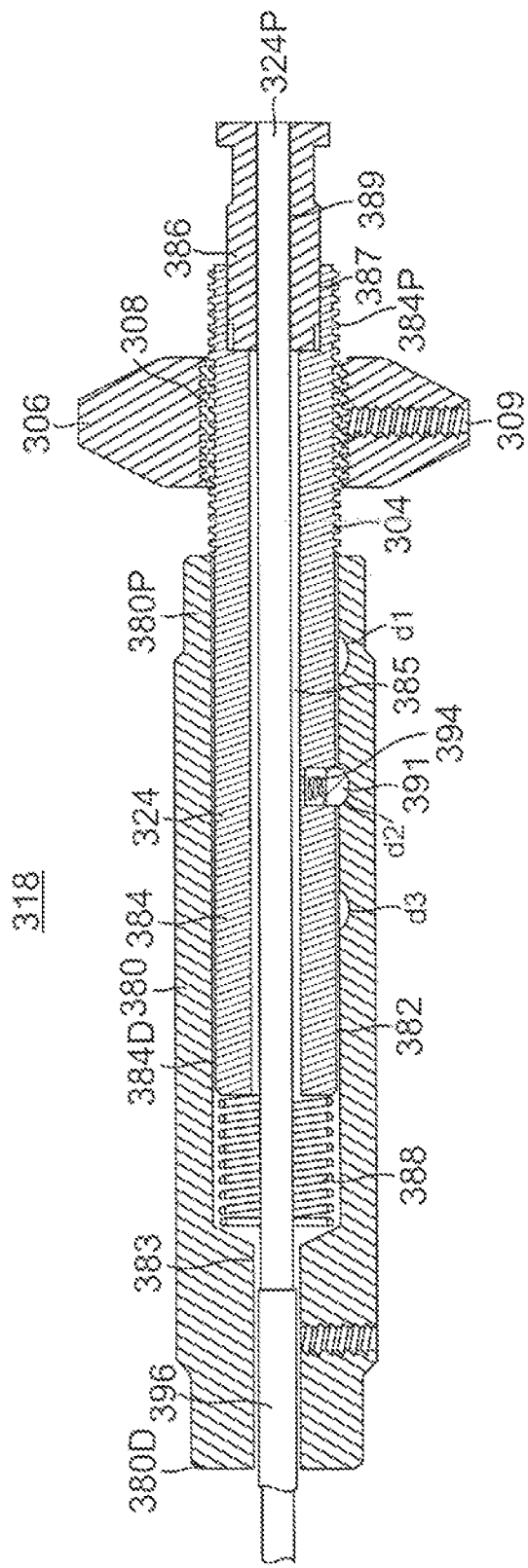
FIG. 11 is a side cross-sectional view of a deflection curvature adjustment handle, in accordance with one embodiment.

In the illustrated embodiment of FIG. 11, the deflection curvature adjustment handle 318 comprises a generally cylindrical outer body 380 having proximal end 380P and distal end 380D, a longitudinal piston chamber 382 extending partially therethrough, and a stiffener passage 383 extending partially therethrough. The piston chamber 382 extends from the proximal end 380P of the outer body 380 partway into the handle 18, but does not extend out the distal end 380D of the outer body. The stiffener passage 383, which has a diameter less than that of the piston chamber 382, extends from the distal end of the piston chamber to the distal end 380D of the outer body 380.

A piston 384, having proximal end 384P and distal end 384D, is slidably mounted within the piston chamber 382. A proximal fitting 386 is mounted in and fixedly attached to the proximal end 384P of the piston 384. The proximal fitting 386 includes a tubular distal region 387 that extends distally from the main body of the proximal fitting and into the proximal end 384P of the piston. The piston 384 has a longitudinal axial passage 385 which is coaxial and connects with an axial passage 389 formed in the proximal fitting 386. The stiffener member 324 has a proximal end 324P that is fixed, e.g., by adhesive, to the proximal fitting 386 and thus coupled to the piston 384 so that movement of the piston results in movement of the stiffener member 324. The stiffener member 324 extends through the axial passages 385 and 389 and out the distal end of the deflection curvature adjustment handle 318.

Figure 12A:
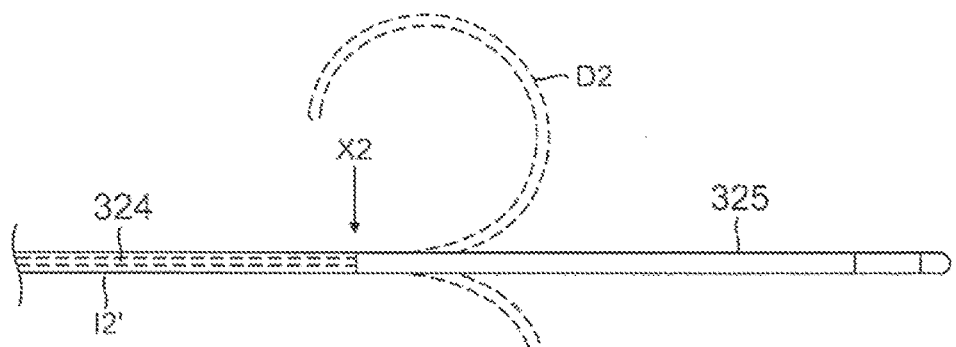
FIG. 12A, FIG. 12B, and FIG. 12C are side views of the catheter shaft of FIG. 10A, as adjusted with different deflection curvatures.
Figure 12B:
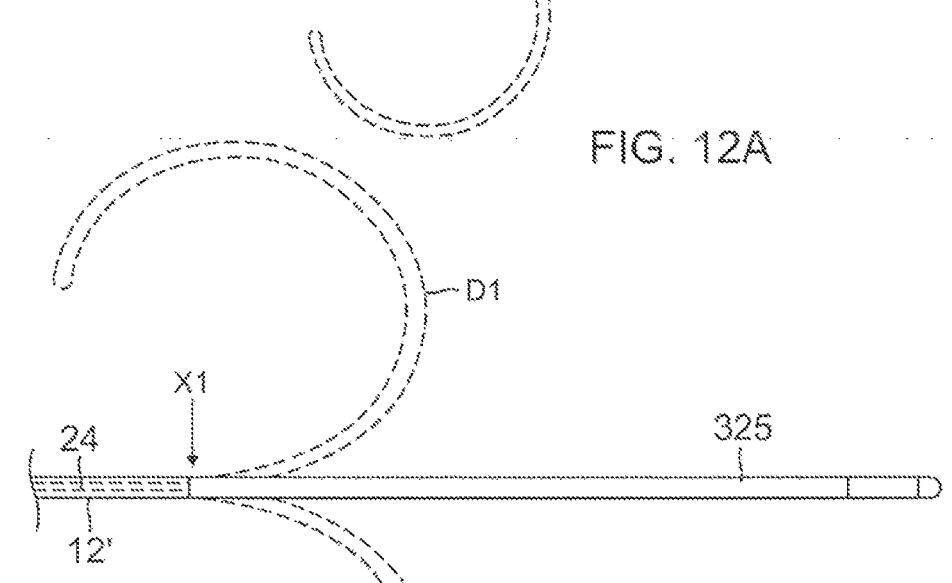
Figure 12C:
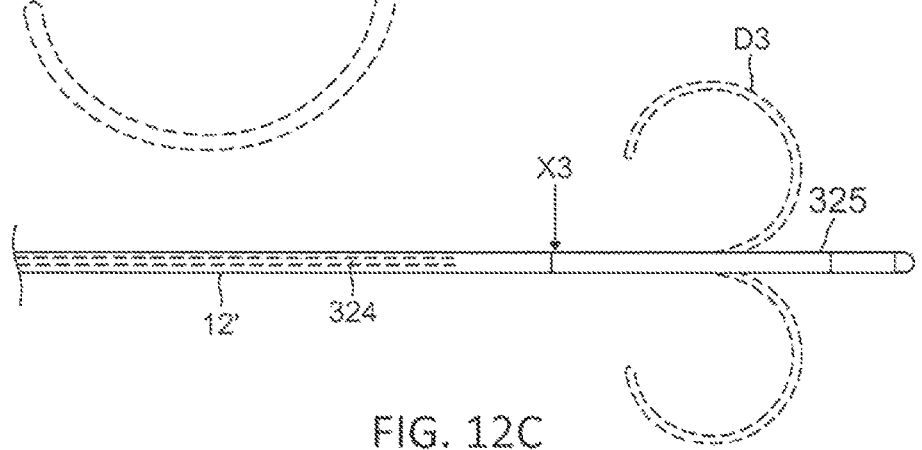

To guide an operator in selecting predetermined types or degrees of deflection curvature of the catheter, the adjustment handle 318 is configured for longitudinal movement of the piston 384 relative to the cylindrical body 380 in a measured or discrete manner. In the illustrated embodiment of FIG. 11, a plurality of recessed detents d1, d2 and d3 are formed on a longitude along an inner radial surface of the piston chamber 382, where each detent is configured to receive and engage with a raised formation, for example, a ridge or, as illustrated, a ball plunger 391 supported and biased by a spring 394 situated in a recess 392, formed on an outer radial surface of the piston 384. Each detent positions the stiffener member 324 within and relative to the catheter shaft 12 such that the distal end of the stiffener member 24 generally sets a location Xi representing a proximal end of the distal deflection section 325 at which its deflection curvature begins. As illustrated in FIG. 12A, FIG. 12B and FIG. 12C, locations X1, X2 and X3 enable the distal deflection section 325 to achieve deflection curvatures D1, D2 and D3, corresponding to the detents d1, d2 and d3, respectively. It is understood that the FIGURES, including those illustrating the detents di and corresponding locations Xi, are not necessarily to scale in relation to each other. It is also understood that the detents may be formed in the outer radial surface of the piston 384, with the raised formation emerging from the inner radial wall of the piston chamber 382.

Optionally, a compression spring 388 may be mounted within the piston chamber 382 to bias movement of the piston relative to the cylindrical body 380 and/or to smooth out this relative movement. The spring 388 may be positioned between the distal end 384D of the piston 384 and the distal end of the piston chamber 382. The compression spring 388 can either be arranged between the piston 384 and outer body 380, or can have one end in contact with or fixed to the piston 384, while the other end is in contact with or fixed to the distal end 380D of the outer body 380.

The proximal end of the piston 384 has a threaded outer surface 304. A circular thumb control 306 is rotatably mounted on the threaded outer surface 304 at proximal end of the piston 384. The thumb control 306 has a threaded inner surface 308 that interacts with the threaded outer surface 304 of the piston 384 so that the longitudinal position of the thumb control 306 relative to the proximal end 380P of the outer body 380 is adjustable. The thumb control 306 acts as a stop, limiting the maximum distance that the piston 384 can be pushed distally into the piston chamber 382, and thus the distance that the stiffener member 324 can be extended distally longitudinally relative to the catheter shaft 12'.

From the deflection curvature adjustment handle 318, the stiffener member 324 extends distally through a protective shaft 396 extending between the distal end of the deflection curvature adjustment handle 318 and proximal end of the deflection control handle 16. The stiffener member 324 extends through the deflection control handle 16 and into the proximal end of the catheter shaft 12'.

Figure 13:
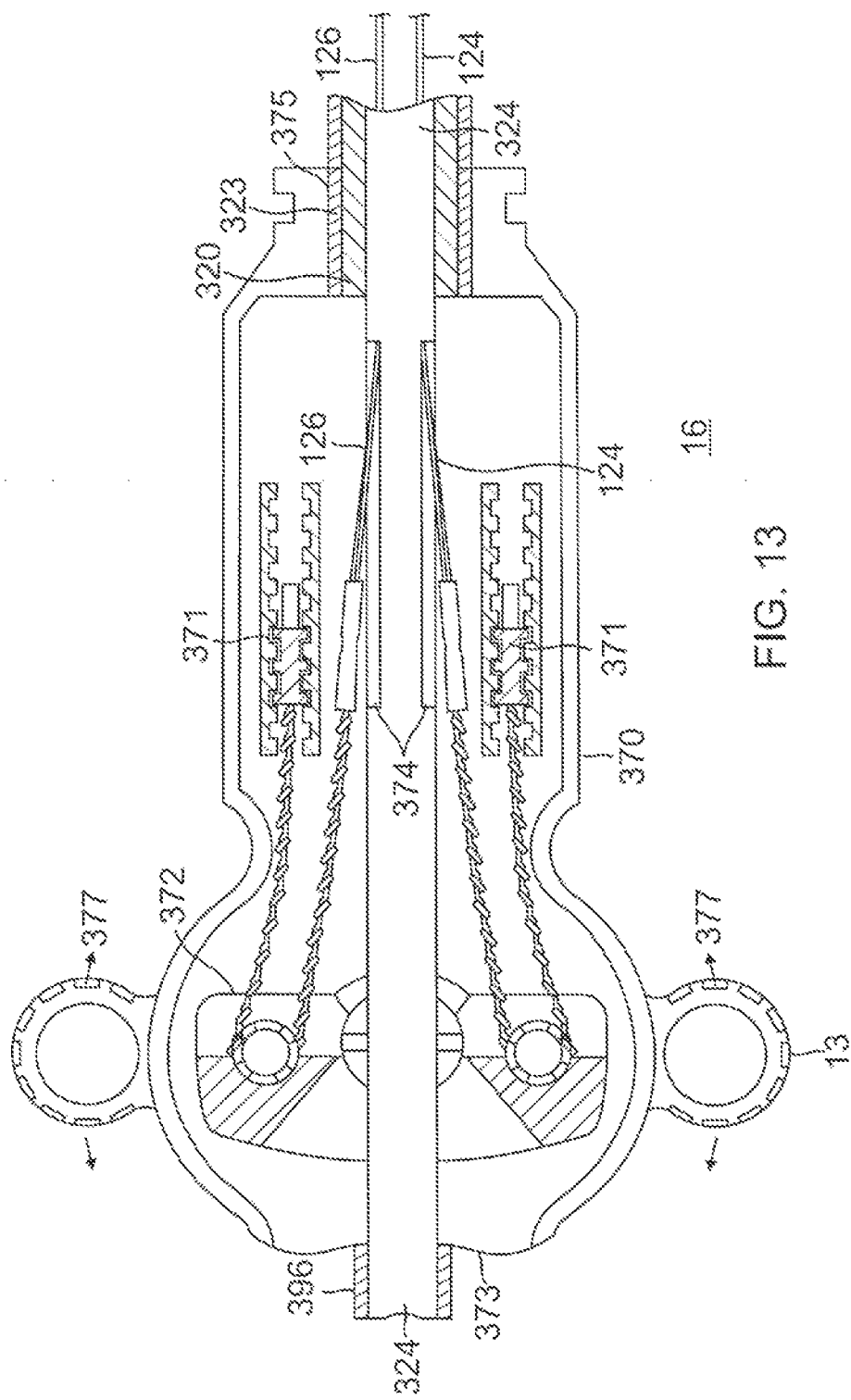
FIG. 13 is a top view of an interior of the catheter rocker handle, according to one embodiment.

As shown in FIG. 13, the deflection control handle 16 has a housing 370 and rocker (pulley) assembly 372 around which the puller wires 124 and 126 are wrapped to redirect their proximal ends into stops 71 that anchor the proximal ends in the control handle 16 at locations distal of the rocker assembly 72. As understood by one of ordinary skill in the art, as an operator pivots or "rocks" the rocker assembly 72 in one direction via the rocker arm 13 (sees arrows 377), the rocker assembly draws proximally on the one puller wire on that side for deflection in that direction while releasing the other wire distally to facilitate the deflection. The stiffener member 324 extends through the length of the housing 370 between a proximal opening 373 and a distal opening 375, and in between the puller wires 124 and 126. Longitudinal openings or slots 374 are formed in the side wall of the stiffener member 324 so that the puller wires 124 and 126 can enter the lumen 325 of the stiffener member 324. The slots 374 have a length sufficient to allow the puller wires to enter the lumen 325 with interfering with the longitudinal movement of the stiffener member 324 relative to the catheter shaft 12'. Suitable deflection control handles are disclosed in U.S. Pat. Nos. 8,617,087 and 8,747,351, the entire disclosures of which are incorporated herein by reference.

In use, an operator either pulls or pushes piston 384 of the adjustment handle 318 to cause longitudinal movement of the piston relative to the outer body 380 from one detent to another detent, as selected by the operator. This movement adjusts the longitudinal position of the stiffener member 324 relative to the catheter shaft 12', thereby allowing the operator to adjust the distal end of the stiffener member and thus the type of deflection curvature of the distal deflection section 325, as shown in FIG. 12A, FIG. 12B and FIG. 12C. By engaging the plunger 391 with a more distal detent, e.g., detent d1, in the adjustment handle 318, as shown in FIG. 11, the piston 384 is set more distally relative to the cylindrical body 380 which positions the distal end of the stiffener member 324 more distally to provide in a smaller or tighter deflection curvature in the distal section 325. In contrast, by engaging the plunger 391 with a more proximal detent, e.g., detent d3, in the adjustment handle 318, the piston 384 is set more proximally relative to the cylindrical body 380 which positions the distal end of the stiffener member 324 more proximally to provide a larger or looser deflection curvature in the distal section 325.

Figure 14:
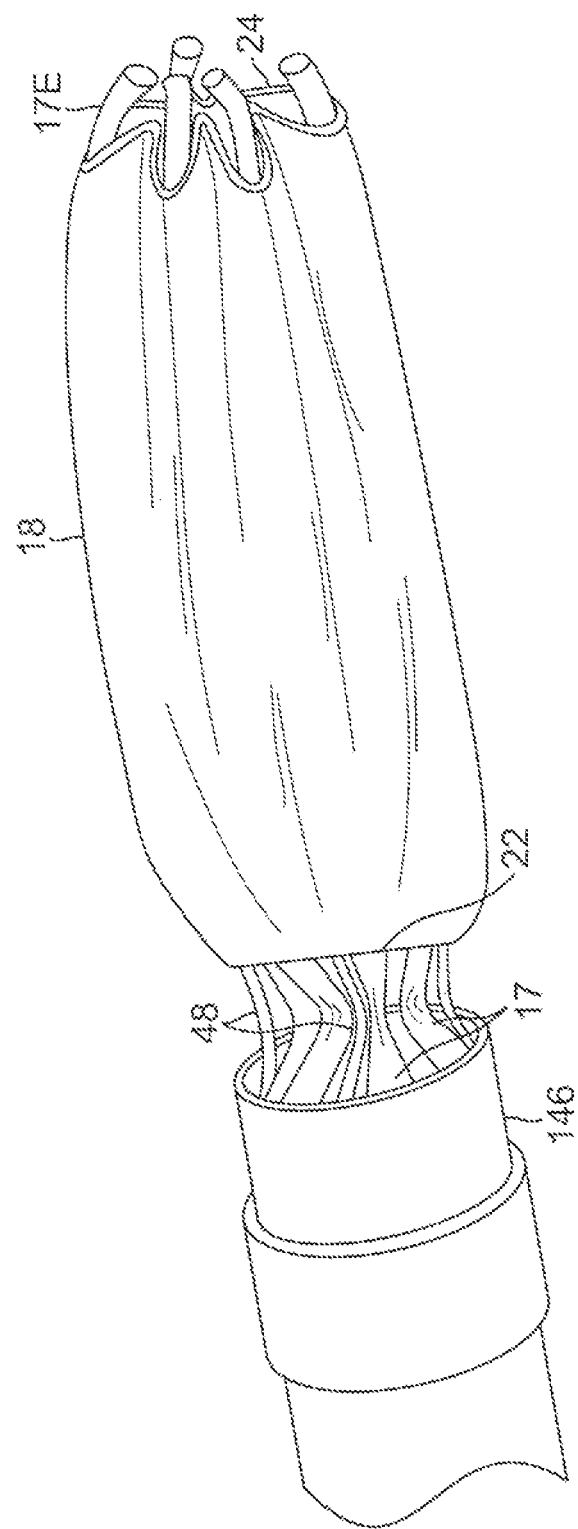
FIG. 14 is a perspective view of the catheter of FIG. 2A in a collapsed configuration.

In use, a suitable guiding sheath (not shown) is inserted into the patient with its distal end positioned at or near a desired tissue location for diagnostics such as mapping and/or treatment such as ablation. An example of a suitable guiding sheath for use in connection with the present invention is the Preface Braided Guiding Sheath, commercially available from Biosense Webster, Inc. (Diamond Bar, Calif.). As shown in FIG. 6A, a guidewire G may also be used to facilitate advancement of the catheter through the patient's vasculature. The catheter 10 is passed through the guiding sheath and advanced therethrough to the desired tissue location. In particular, the spines 17 of the distal assembly 15 are collapsed, as shown in FIG. 14, and generally straightened as much as possible, as shown in FIG. 13, and fed into the proximal end of the guiding sheath. In that regard, the membrane member 18 may be preformed with folds and pleats to facilitate the assembly 15 to assume a collapsed configuration. After the distal assembly 15 has reached the desired tissue location, the guiding sheath is pulled proximally to expose the distal assembly 15. Outside of the guiding sheath, the distal assembly 15 assumes the deployed configuration, as shown, for example, in FIG. 2A.

Figure 6D:
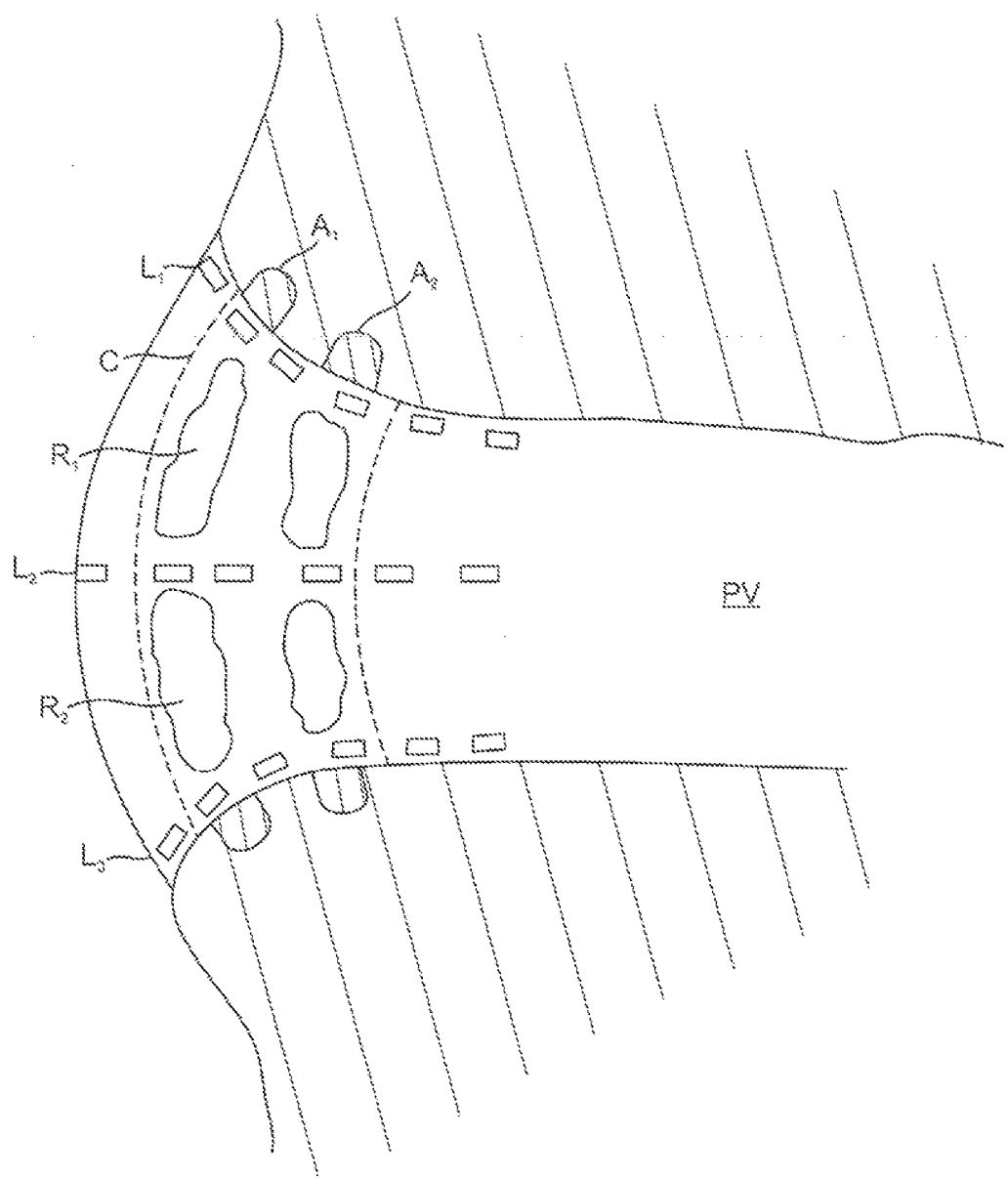
FIG. 6D is a side cross-sectional view of the ostium of FIG. 6A and FIG. 6C.

The operator deflects the distal assembly 15 via the deflection rocker arm 13 of the control handle 16. Where the catheter includes the deflection curvature adjustment handle 318, the operator can adjust the type or tightness of the deflection curvature (see FIG. 12A, FIG. 12B and FIG. 12C) to position the distal assembly 15 over an ostium. As shown in FIG. 3A, FIG. 3B, and FIG. 3C, distal pressure is applied to the control handle 16 and/or the exposed section of the catheter shaft 12 outside of the patient's body to advance the distal assembly into the ostium 28 and the pulmonary vein PV. The distal ends 107E of the spines 17 grip the ostium and the distal curvature 17D comes into contact with the ostium as the proximal curvature 17P increases its curvature away from the longitudinal axis of the catheter. Accordingly, at least a portion of the ring electrodes 20 on the spines 17 are brought into contact with the ostium. Likewise, the membrane member 18 spans across the ostium with its distal surface 25 and surface electrodes 30 in contact with the ostium. With this position and placement of the distal assembly 15, the ring electrodes 20 are able to sense electrical activity along axial lines L (see, e.g., lines L1, L2 and L3 in FIG. 6D) in a circumferential region C of contact between the ostium 28 and the distal assembly 15, while the surface electrodes 30 are able to ablate radial lines R (see, e.g., lines R1 and R2, in FIG. 6D) in the circumferential region C. The operator can rotate the catheter along its length to shift or reposition the distal assembly 15 to sense and ablate along different axial and radial lines in the circumferential region C as needed or desired to form generally contiguous radial regions of ablated tissues A for electrically isolating the left atrium from the pulmonary vein PV.

Where the distal assembly has an inflatable membrane member 18', the operator may accomplish ablation with inflation of the membrane member 18' with cryogenic fluid which distends the member 18, including selective inflation of individual pocket(s) 46 of the membrane 18', to press the surface electrodes 30 on the distal layer 40 against the ostium 28.

In some embodiments, distal and proximal ring electrodes 23 may be provided on the connector tubing 146 (best seen in FIG. 4A) to serve as reference electrodes for visualization of the catheter on a 3-D mapping system, such as CARTO 3 available from Biosense Webster, Inc., which automatically locates the EM position sensor 127, processes reference location values from electrodes 38D and 38P, which are at a constant location from the EM position sensor and determines the location of the spine 17 and visualizes the assembly 15. Likewise, one or more additional ring electrodes may also be provided on any selected spine 17 to serve as a reference electrode for indicating orientation of the distal assembly 15.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale and any feature or combinations of features described in any one embodiment may be incorporated into any other embodiments or combined with any other feature(s) of other embodiments, as desired or needed. For example, any feature described in connection with the distal assembly 15, the membrane member 18, and/or the shaft 12 may be incorporated in the distal assembly 15', the membrane member 18', and/or the shaft 12', and vice versa. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of using a catheter that includes
   an elongated catheter shaft having at least one lumen therethrough, the catheter shaft defining a longitudinal axis; and
   a distal electrode assembly having:
      a plurality of spines situated around the longitudinal axis, each spine having a free distal end and a proximal end anchored in the catheter shaft, each spine having at least one ring electrode; and a membrane member spanning over at least a portion of each spine, the membrane member having a first surface with at least one surface electrode, wherein the membrane member defines a distal concavity when the distal electrode assembly is out of tissue contact and the membrane member defines a distal convexity when the distal electrode assembly is in tissue contact; the method comprising the steps of:

positioning the distal electrode assembly on an ostium with the distal concavity facing the ostium, the distal ends of the spines in contact with tissue generally surrounding the ostium, and the membrane member spanning across the ostium; and advancing the distal electrode assembly into the ostium by pushing distally on the catheter shaft to flex the spines and invert the membrane member within the ostium, thereby placing the at least one surface electrode in contact with the ostium.

2. The method of claim 1, wherein the membrane member is configured for inflation.

3. The method of claim 2, wherein the membrane member is subdivided along the spines to provide separate pockets.

4. The method of claim 1, further comprising inflating the membrane member.

* * * * *